US010648990B2

(12) United States Patent
Sexton et al.

(10) Patent No.: US 10,648,990 B2
(45) Date of Patent: May 12, 2020

(54) DIAGNOSIS AND TREATMENT OF AUTOIMMUNE DISEASES

(71) Applicant: Dyax Corp., Lexington, MA (US)

(72) Inventors: Daniel J. Sexton, Melrose, MA (US); Burt Adelman, Concord, MA (US); Andrew Nixon, Hanover, MA (US)

(73) Assignee: Dyax Corp., Lexington, MA (US)

( * ) Notice: Subject to any disclaimer, the term of this patent is extended or adjusted under 35 U.S.C. 154(b) by 0 days.

(21) Appl. No.: 16/131,781

(22) Filed: Sep. 14, 2018

(65) Prior Publication Data

US 2019/0120862 A1    Apr. 25, 2019

Related U.S. Application Data

(62) Division of application No. 15/030,790, filed as application No. PCT/US2014/061242 on Oct. 17, 2014, now Pat. No. 10,101,344.

(60) Provisional application No. 61/893,542, filed on Oct. 21, 2013.

(51) Int. Cl.
*G01N 33/53* (2006.01)
*G01N 33/86* (2006.01)
*G01N 33/564* (2006.01)

(52) U.S. Cl.
CPC .......... *G01N 33/86* (2013.01); *G01N 33/564* (2013.01); *G01N 2333/745* (2013.01); *G01N 2333/8139* (2013.01); *G01N 2800/065* (2013.01); *G01N 2800/102* (2013.01); *G01N 2800/52* (2013.01); *G01N 2800/56* (2013.01)

(58) Field of Classification Search
None
See application file for complete search history.

(56) References Cited

U.S. PATENT DOCUMENTS

| | | | |
|---|---|---|---|
| 4,882,272 | A | 11/1989 | Scott et al. |
| 4,908,431 | A | 3/1990 | Colman et al. |
| 4,985,354 | A | 1/1991 | Toyomaki et al. |
| 5,025,796 | A | 6/1991 | Hargreaves et al. |
| 5,047,323 | A | 9/1991 | Colman et al. |
| 5,472,945 | A | 12/1995 | Schmaier et al. |
| 6,242,210 | B1 | 6/2001 | Bjoerck et al. |
| 6,913,900 | B2 | 7/2005 | Kaplan et al. |
| 10,101,344 | B2 | 10/2018 | Sexton et al. |
| 2005/0223416 | A1 | 10/2005 | Nuijens et al. |
| 2006/0069020 | A1 | 3/2006 | Blair et al. |
| 2007/0192882 | A1 | 8/2007 | Dewald |
| 2008/0038276 | A1 | 2/2008 | Sinha et al. |
| 2008/0299549 | A1 | 12/2008 | Sorge et al. |
| 2009/0075887 | A1 | 3/2009 | McPherson |
| 2011/0154517 | A1 | 6/2011 | Dewald |
| 2011/0200611 | A1 | 8/2011 | Sexton |
| 2011/0212104 | A1 | 9/2011 | Beaumont et al. |
| 2011/0318359 | A1 | 12/2011 | Feener et al. |
| 2012/0201756 | A1 | 8/2012 | Sexton |
| 2013/0156753 | A1 | 6/2013 | Jin |
| 2014/0128436 | A1 | 5/2014 | Sinha et al. |
| 2015/0362493 | A1 | 12/2015 | Sexton et al. |
| 2016/0252527 | A1 | 9/2016 | Sexton et al. |
| 2018/0306807 | A1 | 10/2018 | Sexton et al. |

FOREIGN PATENT DOCUMENTS

| | | | |
|---|---|---|---|
| CN | 102762203 | A2 | 10/2012 |
| EP | 0210029 | A2 | 1/1987 |
| JP | S63-185398 | A | 7/1988 |
| WO | WO 2006/101387 | A2 | 9/2006 |
| WO | WO 2007/079096 | A2 | 7/2007 |
| WO | WO 2011/075684 | A1 | 6/2011 |
| WO | WO 2012/094587 | A1 | 7/2012 |
| WO | WO 2012/170945 | A2 | 12/2012 |
| WO | WO 2012/170947 | A2 | 12/2012 |
| WO | WO 2014/113712 | A1 | 7/2014 |
| WO | WO 2015/061182 | A1 | 4/2015 |
| WO | WO 2015/061183 | A1 | 4/2015 |

OTHER PUBLICATIONS

[No Author Listed], Image Studio Software Compatible with Mac® Systems Now Available from LI-COR!. BioB Blog. May 2012 8:1-3.
Berrettini et al., Detection of in vitro and in vivo cleavage of high molecular weight kininogen in human plasma by immunoblotting with monoclonal antibodies. Blood. Aug. 1986;68(2):455-62.
Blais et al., The kallikrein-kininogen-kinin system: lessons from the quantification of endogenous kinins. Peptides. Dec. 2000;21(12):1903-40. Review.
Bühler et al., Improved detection of proteolytically cleaved high molecular weight kininogen by immunoblotting using an antiserum against its reduced 47 kDa light chain. Blood Coagul Fibrinolysis. May 1995;6(3):223-32.
Chyung et al., A phase 1 study investigating DX-2930 in healthy subjects. Ann Allergy Asthma Immunol. Oct. 2014;113(4):460-6.e2. doi: 10.1016/j.anai.2014.05.028. Epub Jun. 26, 2014.
Colman et al., Studies on the prekallikrein (kallikreinogen)—kallikrein enzyme system of human plasma. I. Isolation and purification of plasma kallikreins. J Clin Invest. Jan. 1969;48(1):11-22.
Cugno et al., Activation of the coagulation cascade in C1-inhibitor deficiencies. Blood. May 1, 1997;89(9):3213-8.
Cugno et al., Activation of the contact system and fibronolysis in autoimmune acquired angioedema: A rationale for prophylactic use of tranexamic acid. J Allergy Clin Immunol. 1994;93(5):870-876.
Defendi et al., Enzymatic assays for the diagnosis of bradykinin-dependent angioedema. PLoS One. Aug. 5, 2013;8(8):e70140. doi:10.1371/journal.pone.0070140. Print 2013. Erratum in: PLoS One. 2014;9(6):e100345.
Dobo et al., Cleavage of kininogen and subsequent bradykinin release by the complement component: mannose-binding lectin-associated serine protease (MASP)-1. PLoS One. 2011;6(5):e20036. doi: 10.1371/journal.pone.0020036. Epub May 23, 2011.

(Continued)

*Primary Examiner* — Gary Counts
(74) *Attorney, Agent, or Firm* — Wolf, Greenfield & Sacks, P.C.

(57) ABSTRACT

Methods, kits and compositions for diagnosing and treating autoimmue diseases such as rheumatiodi arthritis, Crohn's disease, and ulcerative colitis.

10 Claims, 1 Drawing Sheet
Specification includes a Sequence Listing.

(56) References Cited

OTHER PUBLICATIONS

Faucette et al., A Biomarker Assay for the Detection of Contact System Activation. Blood. 2013;122:2347. Avaible online at http://www.bloodjournal.org/conten/122/21/2347. Last accessed on Mar. 30, 2018.

Gallimore et al., Plasma levels of factor XII, prekallikrein and high molecular weight kininogen in normal blood donors and patients having suffered venous thrombosis. Thromb Res. 2004;114(2):91-6.

Isordia-Salas et al., The mutation Ser511Asn leads to N-glycosylation and increases the cleavage of high molecular weight kininogen in rats genetically susceptible to inflammation. Blood. Oct. 15, 2003;102(8):2835-42.

Isordia-Salas et al., The role of plasma high molecular weight kininogen in experimental intestinal and systemic inflammation. Arch Med Res. Jan.-Feb. 2005;36(1):87-95.

Joseph et al., Studies of the mechanisms of bradykinin generation in hereditary angioedema plasma. Ann Allergy Asthma Immunol. Sep. 2008;101(3):279-86. doi: 10.1016/S1081-1206(10)60493-0.

Katori et al., Evidence for the involvement of a plasma kallikrein-kinin system in the immediate hypotension produced by endotoxin in anaesthetized rats. Br J Pharmacol. Dec. 1989;98(4):1383-91.

Kerbiriou-Nabias et al., Radioimmunoassays of human high and low molecular weight kininogens in plasmas and platelets. Br J Haematol. Feb. 1984;56(2):273-86.

Khan et al., High-molecular-weight kininogen fragments stimulate the secretion of cytokines and chemokines through uPAR, Mac-1, and gC1qR in monocytes. Arterioscler Thromb Vasc Biol. Oct. 2006;26(10):2260-6. Epub Aug. 10, 2006. Erratum in: Arterioscler Thromb Vasc Biol. Nov. 2006;26(11):e146.

Ladner et al., Discovery of Ecallantide: A Potent and Selective Inhibitor of Plasma Kallikrein. J Allergy and Clinical Immuno. Jan. 1, 2007;119(1):S312.

Merlo et al., Elevated levels of plasma prekallikrein, high molecular weight kininogen and factor XI in coronary heart disease. Atherosclerosis. Apr. 2002;161(2):261-7.

Nguyen et al., The Simple Western™: a gel-free, blot-free, hands-free Western blotting reinvention. Nature Methods. Oct. 28, 2011;8:5-6.

Nielsen et al., Hereditary angio-oedema: new clinical observations and autoimmune screening, complement and kallikrein-kinin analyses. J Intern Med. Feb. 1996;239(2):119-30.

Page et al., An autoantibody to human plasma prekallikrein blocks activation of the contact system. Br J Haematol. May 1994;87(1):81-6.

Phipps et al., Plasma kallikrein mediates angiotensin II type 1 receptor-stimulated retinal vascular permeability. Hypertension. Feb. 2009;53(2):175-81. doi: 10.1161/HYPERTENSIONAHA.108.117663.

Raymond et al., Quantification of des-Arg9-bradykinin using a chemiluminescence enzyme immunoassay: application to its kinetic profile during plasma activation. J Immunol Methods. Mar. 27, 1995;180(2):247-57.

Reddigari et al., Cleavage of human high-molecular weight kininogen by purified kallikreins and upon contact activation of plasma. Blood. May 1988;71(5):1334-40.

Reddigari et al., Monoclonal antibody to human high-molecular-weight kininogen recognizes its prekallikrein binding site and inhibits its coagulant activity. Blood. Aug. 1, 1989;74(2):695-702.

Reddigari et al., Quantification of human high molecular weight kininogen by immunoblotting with a monoclonal anti-light chain antibody. J Immunol Methods. Apr. 21, 1989;119(1):19-25.

Schmaier et al., Determination of the bifunctional properties of high molecular weight kininogen by studies with monoclonal antibodies directed to each of its chains. J Biol Chem. Jan. 25, 1987;262(3):1405-11.

Schousboe et al., High molecular weight kininogen binds to laminin—characterization and kinetic analysis.FEBS J. Sep. 2009;276(18):5228-38. doi: 10.1111/j.1742-4658.2009.07218.x. Epub Aug. 19, 2009.

Scott et al., A new assay for high molecular weight kininogen in human plasma using a chromogenic substrate. Thromb Res. Dec. 15, 1987;48(6):685-700.

Torzewski et al., Animal Models of c-Reactive Protein. Hindawi Publishing Corpl, Mediators of Inflammation. 2014:1-7.

Van Der Vekens et al., Human and equine cardiovascular endrocrinology: beware to compare. Cardivasacular Endicronology. 2013;2(4):67-76.

Williams et al., DX-88 and HAE: a developmental perspective. Transfus Apher Sci. Dec. 2003;29(3):255-8.

Zhang et al., Two-chain high molecular weight kininogen induces endothelial cell apoptosis and inhibits angiogenesis: partial activity within domain 5. FASEB J. Dec. 2000;14(15):2589-600.

U.S. Appl. No. 15/769,237, filed Apr. 18, 2018, Sexton et al.

PCT/US2016/057640, Jan. 26, 2017, International Search Report and Written Opinion.

PCT/US2016/057640, May 3, 2018, International Preliminary Report on Patentability.

EP 18186356.4, Jan. 18, 2019, Extended European Search Report.

[No Author Listed], Mouse High Molecular Weight Kininogen (HMWK) ELISA Kit (Cat. No. BMS089195). MyBiosource Datasheet. Jan. 2, 1984. Retrieved from <https://www.mybiosource.com/prods/ELIS-A-Kit/Mouse/High-Molecular-Weight-Kinogen/HMWK/datasheet.php?products_id=89195> on Dec. 13, 2018. 4 pages.

Cugno et al., Activation of factor XII and cleavage of high molecular weight kininogen during acute attacks in hereditary and acquired C1-inhibitor deficiencies. Immunopharmacology. Jun. 1996;33(1-3):361-4.

Devani et al., Kallikrein-kinin system activation in Crohn's disease: differences in intestinal and systemic markers. Am J Gastroenterol. Aug. 2002;97(8):2026-32.

Ishiguro et al., Mapping of functional domains of human high molecular weight and low molecular weight kininogens using murine monoclonal antibodies. Biochemistry. Nov. 3, 1987;26(22):7021-9.

Scott et al., Sensitive antigenic determinations of high molecular weight kininogen performed by covalent coupling of capture antibody. J Lab Clin Med. Jan. 1992;119(1):77-86. Abstract only.

Sexton et al., Discovery and Characterization of a Fully Human Monoclonal Antibody Inhibitor of Plasma Kallikrein for the Treatment of Plamsa Kallikrein-Mediated Edema. J. Allergy Clin. Immunol. Feb. 2013;131(2):AB32.

Syvänen et al., A radioimmunoassay for the detection of molecular forms of human plasma kininogen. FEBS Lett. Jul. 6, 1981;129(2):241-5.

Uchida et al., Differential assay method for high molecular weight and low molecular weight kininogens. Thromb Res. 1979;15(1-2):127-34.

Veloso et al., A monoclonal anti-human plasma prekallikrein antibody that inhibits activation of prekallikrein by factor XIIa on a surface. Blood. Oct. 1987;70(4):1053-62.

U.S. Appl. No. 15/030,790, dated Apr. 20, 2016, Granted, U.S. Pat. No. 10,101,344.

U.S. Appl. No. 14/761,690, dated Jul. 17, 2015, Published, 2015-0362493.

U.S. Appl. No. 15/030,811, dated Apr. 20, 2016, Published, 2016-0252527.

EP 14855002.3, dated Feb. 20, 2017, Extended European Search Report.

PCT/US2014/061242, dated Feb. 3, 2015, International Search Report and Written Opinion.

PCT/US2014/061242, dated May 6, 2016, International Preliminary Report on Patentability.

EP 147404440.6, dated Jun. 17, 2016, Extended European Search Report.

PCT/US2014/012107, dated Apr. 14, 2014, International Search Report and Written Opinion.

PCT/US2014/012107, dated Jun. 30, 2015, International Preliminary Report on Patentability.

EP 14856778.7, dated Feb. 28, 2017, Partial Supplmentary European Search Report.

EP14856778.7, dated Jun. 16, 2017, Supplementary European Search Report.

(56) References Cited

OTHER PUBLICATIONS

PCT/US2014/061247, dated Feb. 4, 2015, International Search Report and Written Opinion.
PCT/US2014/061247, dated May 6, 2016, International Preliminary Report on Patentability.

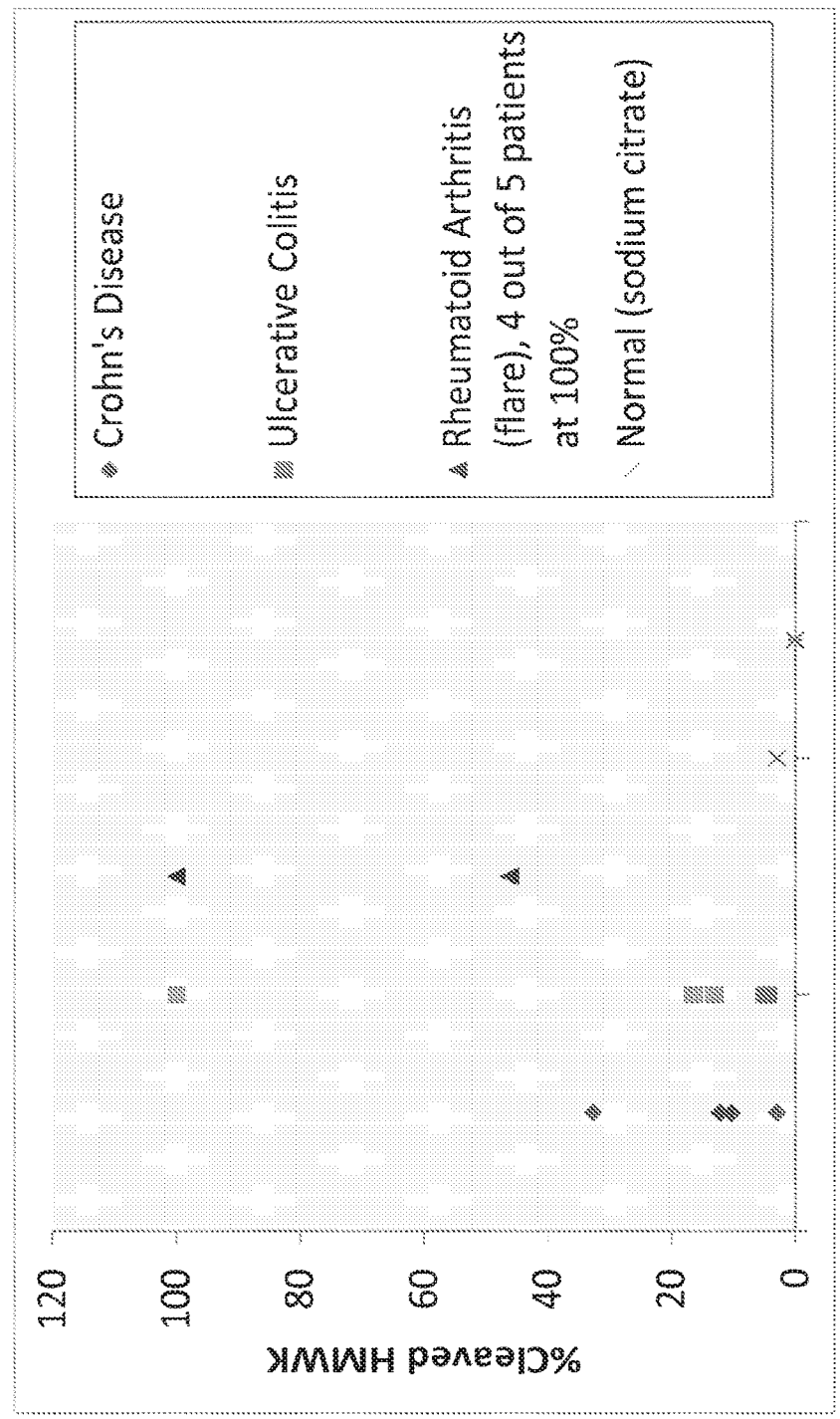

SEQUENCE LISTING

```
<160> NUMBER OF SEQ ID NOS: 7

<210> SEQ ID NO 1
<211> LENGTH: 58
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(4)
<223> OTHER INFORMATION: Xaa can be any naturally occurring amino acid
      except for Cys
<220> FEATURE:
<221> NAME/KEY: misc_feature
<222> LOCATION: (6)..(11)
<223> OTHER INFORMATION: Xaa can be any naturally occurring amino acid
      except for Cys
<220> FEATURE:
<221> NAME/KEY: misc_feature
<222> LOCATION: (13)..(13)
<223> OTHER INFORMATION: Xaa can be any naturally occurring amino acid
      except for Cys
<220> FEATURE:
<221> NAME/KEY: misc_feature
<222> LOCATION: (15)..(29)
<223> OTHER INFORMATION: Xaa can be any naturally occurring amino acid
      except for Cys
<220> FEATURE:
<221> NAME/KEY: misc_feature
<222> LOCATION: (31)..(32)
<223> OTHER INFORMATION: Xaa can be any naturally occurring amino acid
      except for Cys
<220> FEATURE:
```

```
<221> NAME/KEY: misc_feature
<222> LOCATION: (34)..(35)
<223> OTHER INFORMATION: Xaa can be any naturally occurring amino acid
      except for Cys
<220> FEATURE:
<221> NAME/KEY: misc_feature
<222> LOCATION: (39)..(50)
<223> OTHER INFORMATION: Xaa can be any naturally occurring amino acid
      except for Cys
<220> FEATURE:
<221> NAME/KEY: misc_feature
<222> LOCATION: (52)..(54)
<223> OTHER INFORMATION: Xaa can be any naturally occurring amino acid
      except for Cys
<220> FEATURE:
<221> NAME/KEY: misc_feature
<222> LOCATION: (56)..(58)
<223> OTHER INFORMATION: Xaa can be any naturally occurring amino acid
      except for Cys

<400> SEQUENCE: 1

Xaa Xaa Xaa Xaa Cys Xaa Xaa Xaa Xaa Xaa Gly Xaa Cys Xaa Xaa
1               5                   10                  15

Xaa Xaa Xaa Xaa Xaa Xaa Xaa Xaa Xaa Xaa Xaa Xaa Xaa Cys Xaa Xaa
            20                  25                  30

Phe Xaa Xaa Gly Gly Cys Xaa Xaa Xaa Xaa Xaa Xaa Xaa Xaa
        35                  40                  45

Xaa Xaa Cys Xaa Xaa Xaa Cys Xaa Xaa Xaa
    50                  55

<210> SEQ ID NO 2
<211> LENGTH: 60
<212> TYPE: PRT
<213> ORGANISM: Artificial Sequence
<220> FEATURE:
<223> OTHER INFORMATION: Synthetic Polypeptide

<400> SEQUENCE: 2

Glu Ala Met His Ser Phe Cys Ala Phe Lys Ala Asp Asp Gly Pro Cys
1               5                   10                  15

Arg Ala Ala His Pro Arg Trp Phe Phe Asn Ile Phe Thr Arg Gln Cys
            20                  25                  30

Glu Glu Phe Ile Tyr Gly Gly Cys Glu Gly Asn Gln Asn Arg Phe Glu
        35                  40                  45

Ser Leu Glu Glu Cys Lys Lys Met Cys Thr Arg Asp
    50                  55                  60

<210> SEQ ID NO 3
<211> LENGTH: 638
<212> TYPE: PRT
<213> ORGANISM: Homo sapiens

<400> SEQUENCE: 3

Met Ile Leu Phe Lys Gln Ala Thr Tyr Phe Ile Ser Leu Phe Ala Thr
1               5                   10                  15

Val Ser Cys Gly Cys Leu Thr Gln Leu Tyr Glu Asn Ala Phe Phe Arg
            20                  25                  30

Gly Gly Asp Val Ala Ser Met Tyr Thr Pro Asn Ala Gln Tyr Cys Gln
        35                  40                  45

Met Arg Cys Thr Phe His Pro Arg Cys Leu Leu Phe Ser Phe Leu Pro
    50                  55                  60

Ala Ser Ser Ile Asn Asp Met Glu Lys Arg Phe Gly Cys Phe Leu Lys
65                  70                  75                  80
```

```
Asp Ser Val Thr Gly Thr Leu Pro Lys Val His Arg Thr Gly Ala Val
                 85                  90                  95

Ser Gly His Ser Leu Lys Gln Cys Gly His Gln Ile Ser Ala Cys His
            100                 105                 110

Arg Asp Ile Tyr Lys Gly Val Asp Met Arg Gly Val Asn Phe Asn Val
            115                 120                 125

Ser Lys Val Ser Ser Val Glu Glu Cys Gln Lys Arg Cys Thr Ser Asn
        130                 135                 140

Ile Arg Cys Gln Phe Phe Ser Tyr Ala Thr Gln Thr Phe His Lys Ala
145                 150                 155                 160

Glu Tyr Arg Asn Asn Cys Leu Leu Lys Tyr Ser Pro Gly Gly Thr Pro
                165                 170                 175

Thr Ala Ile Lys Val Leu Ser Asn Val Glu Ser Gly Phe Ser Leu Lys
            180                 185                 190

Pro Cys Ala Leu Ser Glu Ile Gly Cys His Met Asn Ile Phe Gln His
        195                 200                 205

Leu Ala Phe Ser Asp Val Asp Val Ala Arg Val Leu Thr Pro Asp Ala
210                 215                 220

Phe Val Cys Arg Thr Ile Cys Thr Tyr His Pro Asn Cys Leu Phe Phe
225                 230                 235                 240

Thr Phe Tyr Thr Asn Val Trp Lys Ile Glu Ser Gln Arg Asn Val Cys
                245                 250                 255

Leu Leu Lys Thr Ser Glu Ser Gly Thr Pro Ser Ser Thr Pro Gln
            260                 265                 270

Glu Asn Thr Ile Ser Gly Tyr Ser Leu Leu Thr Cys Lys Arg Thr Leu
                275                 280                 285

Pro Glu Pro Cys His Ser Lys Ile Tyr Pro Gly Val Asp Phe Gly Gly
        290                 295                 300

Glu Glu Leu Asn Val Thr Phe Val Lys Gly Val Asn Val Cys Gln Glu
305                 310                 315                 320

Thr Cys Thr Lys Met Ile Arg Cys Gln Phe Phe Thr Tyr Ser Leu Leu
                325                 330                 335

Pro Glu Asp Cys Lys Glu Glu Lys Cys Lys Cys Phe Leu Arg Leu Ser
        340                 345                 350

Met Asp Gly Ser Pro Thr Arg Ile Ala Tyr Gly Thr Gln Gly Ser Ser
            355                 360                 365

Gly Tyr Ser Leu Arg Leu Cys Asn Thr Gly Asp Asn Ser Val Cys Thr
        370                 375                 380

Thr Lys Thr Ser Thr Arg Ile Val Gly Gly Thr Asn Ser Ser Trp Gly
385                 390                 395                 400

Glu Trp Pro Trp Gln Val Ser Leu Gln Val Lys Leu Thr Ala Gln Arg
                405                 410                 415

His Leu Cys Gly Gly Ser Leu Ile Gly His Gln Trp Val Leu Thr Ala
            420                 425                 430

Ala His Cys Phe Asp Gly Leu Pro Leu Gln Asp Val Trp Arg Ile Tyr
        435                 440                 445

Ser Gly Ile Leu Asn Leu Ser Asp Ile Thr Lys Asp Thr Pro Phe Ser
        450                 455                 460

Gln Ile Lys Glu Ile Ile Ile His Gln Asn Tyr Lys Val Ser Glu Gly
465                 470                 475                 480

Asn His Asp Ile Ala Leu Ile Lys Leu Gln Ala Pro Leu Asn Tyr Thr
                485                 490                 495

Glu Phe Gln Lys Pro Ile Cys Leu Pro Ser Lys Gly Asp Thr Ser Thr
```

```
                      500                 505                 510
Ile Tyr Thr Asn Cys Trp Val Thr Gly Trp Gly Phe Ser Lys Glu Lys
            515                 520                 525

Gly Glu Ile Gln Asn Ile Leu Gln Lys Val Asn Ile Pro Leu Val Thr
            530                 535                 540

Asn Glu Glu Cys Gln Lys Arg Tyr Gln Asp Tyr Lys Ile Thr Gln Arg
545                 550                 555                 560

Met Val Cys Ala Gly Tyr Lys Glu Gly Lys Asp Ala Cys Lys Gly
            565                 570                 575

Asp Ser Gly Gly Pro Leu Val Cys Lys His Asn Gly Met Trp Arg Leu
            580                 585                 590

Val Gly Ile Thr Ser Trp Gly Glu Gly Cys Ala Arg Arg Glu Gln Pro
            595                 600                 605

Gly Val Tyr Thr Lys Val Ala Glu Tyr Met Asp Trp Ile Leu Glu Lys
            610                 615                 620

Thr Gln Ser Ser Asp Gly Lys Ala Gln Met Gln Ser Pro Ala
625                 630                 635

<210> SEQ ID NO 4
<211> LENGTH: 262
<212> TYPE: PRT
<213> ORGANISM: Homo sapiens

<400> SEQUENCE: 4

Met Trp Phe Leu Val Leu Cys Leu Ala Leu Ser Leu Gly Gly Thr Gly
1               5                   10                  15

Ala Ala Pro Pro Ile Gln Ser Arg Ile Val Gly Gly Trp Glu Cys Glu
            20                  25                  30

Gln His Ser Gln Pro Trp Gln Ala Ala Leu Tyr His Phe Ser Thr Phe
        35                  40                  45

Gln Cys Gly Gly Ile Leu Val His Arg Gln Trp Val Leu Thr Ala Ala
    50                  55                  60

His Cys Ile Ser Asp Asn Tyr Gln Leu Trp Leu Gly Arg His Asn Leu
65                  70                  75                  80

Phe Asp Asp Glu Asn Thr Ala Gln Phe Val His Val Ser Glu Ser Phe
                85                  90                  95

Pro His Pro Gly Phe Asn Met Ser Leu Leu Glu Asn His Thr Arg Gln
            100                 105                 110

Ala Asp Glu Asp Tyr Ser His Asp Leu Met Leu Leu Arg Leu Thr Glu
        115                 120                 125

Pro Ala Asp Thr Ile Thr Asp Ala Val Lys Val Val Glu Leu Pro Thr
    130                 135                 140

Gln Glu Pro Glu Val Gly Ser Thr Cys Leu Ala Ser Gly Trp Gly Ser
145                 150                 155                 160

Ile Glu Pro Glu Asn Phe Ser Phe Pro Asp Asp Leu Gln Cys Val Asp
                165                 170                 175

Leu Lys Ile Leu Pro Asn Asp Glu Cys Lys Lys Val His Val Gln Lys
            180                 185                 190

Val Thr Asp Phe Met Leu Cys Val Gly His Leu Glu Gly Gly Lys Asp
        195                 200                 205

Thr Cys Val Gly Asp Ser Gly Gly Pro Leu Met Cys Asp Gly Val Leu
    210                 215                 220

Gln Gly Val Thr Ser Trp Gly Tyr Val Pro Cys Gly Thr Pro Asn Lys
225                 230                 235                 240
```

```
Pro Ser Val Ala Val Arg Val Leu Ser Tyr Val Lys Trp Ile Glu Asp
            245                 250                 255
Thr Ile Ala Glu Asn Ser
            260

<210> SEQ ID NO 5
<211> LENGTH: 644
<212> TYPE: PRT
<213> ORGANISM: Homo sapiens

<400> SEQUENCE: 5

Met Lys Leu Ile Thr Ile Leu Phe Leu Cys Ser Arg Leu Leu Leu Ser
1               5                   10                  15
Leu Thr Gln Glu Ser Gln Ser Glu Glu Ile Asp Cys Asn Asp Lys Asp
            20                  25                  30
Leu Phe Lys Ala Val Asp Ala Ala Leu Lys Lys Tyr Asn Ser Gln Asn
        35                  40                  45
Gln Ser Asn Asn Gln Phe Val Leu Tyr Arg Ile Thr Glu Ala Thr Lys
    50                  55                  60
Thr Val Gly Ser Asp Thr Phe Tyr Ser Phe Lys Tyr Glu Ile Lys Glu
65                  70                  75                  80
Gly Asp Cys Pro Val Gln Ser Gly Lys Thr Trp Gln Asp Cys Glu Tyr
                85                  90                  95
Lys Asp Ala Ala Lys Ala Ala Thr Gly Glu Cys Thr Ala Thr Val Gly
            100                 105                 110
Lys Arg Ser Ser Thr Lys Phe Ser Val Ala Thr Gln Thr Cys Gln Ile
        115                 120                 125
Thr Pro Ala Glu Gly Pro Val Val Thr Ala Gln Tyr Asp Cys Leu Gly
    130                 135                 140
Cys Val His Pro Ile Ser Thr Gln Ser Pro Asp Leu Glu Pro Ile Leu
145                 150                 155                 160
Arg His Gly Ile Gln Tyr Phe Asn Asn Asn Thr Gln His Ser Ser Leu
                165                 170                 175
Phe Met Leu Asn Glu Val Lys Arg Ala Gln Arg Gln Val Val Ala Gly
            180                 185                 190
Leu Asn Phe Arg Ile Thr Tyr Ser Ile Val Gln Thr Asn Cys Ser Lys
        195                 200                 205
Glu Asn Phe Leu Phe Leu Thr Pro Asp Cys Lys Ser Leu Trp Asn Gly
    210                 215                 220
Asp Thr Gly Glu Cys Thr Asp Asn Ala Tyr Ile Asp Ile Gln Leu Arg
225                 230                 235                 240
Ile Ala Ser Phe Ser Gln Asn Cys Asp Ile Tyr Pro Gly Lys Asp Phe
                245                 250                 255
Val Gln Pro Pro Thr Lys Ile Cys Val Gly Cys Pro Arg Asp Ile Pro
            260                 265                 270
Thr Asn Ser Pro Glu Leu Glu Glu Thr Leu Thr His Thr Ile Thr Lys
        275                 280                 285
Leu Asn Ala Glu Asn Asn Ala Thr Phe Tyr Phe Lys Ile Asp Asn Val
    290                 295                 300
Lys Lys Ala Arg Val Gln Val Val Ala Gly Lys Lys Tyr Phe Ile Asp
305                 310                 315                 320
Phe Val Ala Arg Glu Thr Thr Cys Ser Lys Glu Ser Asn Glu Glu Leu
                325                 330                 335
Thr Glu Ser Cys Glu Thr Lys Lys Leu Gly Gln Ser Leu Asp Cys Asn
            340                 345                 350
```

Ala Glu Val Tyr Val Val Pro Trp Glu Lys Lys Ile Tyr Pro Thr Val
              355                 360                 365

Asn Cys Gln Pro Leu Gly Met Ile Ser Leu Met Lys Arg Pro Pro Gly
        370                 375                 380

Phe Ser Pro Phe Arg Ser Arg Ile Gly Glu Ile Lys Glu Glu Thr
385                 390                 395                 400

Thr Val Ser Pro Pro His Thr Ser Met Ala Pro Ala Gln Asp Glu Glu
                405                 410                 415

Arg Asp Ser Gly Lys Glu Gln Gly His Thr Arg Arg His Asp Trp Gly
            420                 425                 430

His Glu Lys Gln Arg Lys His Asn Leu Gly His Gly His Lys His Glu
        435                 440                 445

Arg Asp Gln Gly His Gly His Gln Arg Gly His Gly Leu Gly His Gly
    450                 455                 460

His Glu Gln Gln His Gly Leu Gly His Gly His Lys Phe Lys Leu Asp
465                 470                 475                 480

Asp Asp Leu Glu His Gln Gly Gly His Val Leu Asp His Gly His Lys
                485                 490                 495

His Lys His Gly His Gly His Lys His Lys Asn Lys Gly Lys Lys
            500                 505                 510

Asn Gly Lys His Asn Gly Trp Lys Thr Glu His Leu Ala Ser Ser Ser
        515                 520                 525

Glu Asp Ser Thr Thr Pro Ser Ala Gln Thr Gln Glu Lys Thr Glu Gly
    530                 535                 540

Pro Thr Pro Ile Pro Ser Leu Ala Lys Pro Gly Val Thr Val Thr Phe
545                 550                 555                 560

Ser Asp Phe Gln Asp Ser Asp Leu Ile Ala Thr Met Met Pro Pro Ile
                565                 570                 575

Ser Pro Ala Pro Ile Gln Ser Asp Asp Trp Ile Pro Asp Ile Gln
            580                 585                 590

Ile Asp Pro Asn Gly Leu Ser Phe Asn Pro Ile Ser Asp Phe Pro Asp
        595                 600                 605

Thr Thr Ser Pro Lys Cys Pro Gly Arg Pro Trp Lys Ser Val Ser Glu
    610                 615                 620

Ile Asn Pro Thr Thr Gln Met Lys Glu Ser Tyr Tyr Phe Asp Leu Thr
625                 630                 635                 640

Asp Gly Leu Ser

<210> SEQ ID NO 6
<211> LENGTH: 362
<212> TYPE: PRT
<213> ORGANISM: Artificial Sequence
<220> FEATURE:
<223> OTHER INFORMATION: Synthetic Polypeptide

<400> SEQUENCE: 6

Gln Glu Ser Gln Ser Glu Gly Ile Asp Cys Asn Asp Lys Asp Leu Phe
1               5                   10                  15

Lys Ala Val Asp Ala Ala Leu Lys Lys Tyr Asn Ser Gln Asn Gln Ser
            20                  25                  30

Asn Asn Gln Phe Val Leu Tyr Arg Ile Thr Glu Ala Thr Lys Thr Val
        35                  40                  45

Gly Ser Asp Thr Phe Tyr Ser Phe Lys Tyr Glu Ile Lys Glu Gly Asp
    50                  55                  60

```
Cys Pro Val Gln Ser Gly Lys Thr Trp Gln Asp Cys Glu Tyr Lys Asp
 65                  70                  75                  80

Ala Ala Lys Ala Ala Thr Gly Glu Cys Thr Ala Thr Val Gly Lys Arg
                 85                  90                  95

Ser Ser Thr Lys Phe Ser Val Ala Thr Gln Thr Cys Gln Ile Thr Pro
            100                 105                 110

Ala Glu Gly Pro Val Val Thr Ala Gln Tyr Asp Cys Leu Gly Cys Val
        115                 120                 125

His Pro Ile Ser Thr Gln Ser Pro Asp Leu Glu Pro Ile Leu Arg His
    130                 135                 140

Gly Ile Gln Tyr Phe Asn Asn Asn Thr Gln His Ser Ser Leu Phe Met
145                 150                 155                 160

Leu Asn Glu Val Lys Arg Ala Gln Arg Gln Val Val Ala Gly Leu Asn
                165                 170                 175

Phe Arg Ile Thr Tyr Ser Ile Val Gln Thr Asn Cys Ser Lys Glu Asn
            180                 185                 190

Phe Leu Phe Leu Thr Pro Asp Cys Lys Ser Leu Trp Asn Gly Asp Thr
        195                 200                 205

Gly Glu Cys Thr Asp Asn Ala Tyr Ile Asp Ile Gln Leu Arg Ile Ala
    210                 215                 220

Ser Phe Ser Gln Asn Cys Asp Ile Tyr Pro Gly Lys Asp Phe Val Gln
225                 230                 235                 240

Pro Pro Thr Lys Ile Cys Val Gly Cys Pro Arg Asp Ile Pro Thr Asn
                245                 250                 255

Ser Pro Glu Leu Glu Glu Thr Leu Thr His Thr Ile Thr Lys Leu Asn
            260                 265                 270

Ala Glu Asn Asn Ala Thr Phe Tyr Phe Lys Ile Asp Asn Val Lys Lys
        275                 280                 285

Ala Arg Val Gln Val Val Ala Gly Lys Lys Tyr Phe Ile Asp Phe Val
    290                 295                 300

Ala Arg Glu Thr Thr Cys Ser Lys Glu Ser Asn Glu Glu Leu Thr Glu
305                 310                 315                 320

Ser Cys Glu Thr Lys Lys Leu Gly Gln Ser Leu Asp Cys Asn Ala Glu
                325                 330                 335

Val Tyr Val Val Pro Trp Glu Lys Lys Ile Tyr Pro Thr Val Asn Cys
            340                 345                 350

Gln Pro Leu Gly Met Ile Ser Leu Met Lys
        355                 360
```

<210> SEQ ID NO 7
<211> LENGTH: 255
<212> TYPE: PRT
<213> ORGANISM: Artificial Sequence
<220> FEATURE:
<223> OTHER INFORMATION: Synthetic Polypeptide

<400> SEQUENCE: 7

```
Ser Ser Arg Ile Gly Glu Ile Lys Glu Glu Thr Val Ser Pro Pro
 1               5                  10                  15

His Thr Ser Met Ala Pro Ala Gln Asp Glu Glu Arg Asp Ser Gly Lys
                 20                  25                  30

Glu Gln Gly His Thr Arg Arg His Asp Trp Gly His Glu Lys Gln Arg
            35                  40                  45

Lys His Asn Leu Gly His Gly Lys His Glu Arg Asp Gln Gly His
    50                  55                  60
```

```
                         -continued
Gly His Gln Arg Gly His Gly Leu Gly His Gly His Glu Gln Gln His
 65              70              75              80

Gly Leu Gly His Gly His Lys Phe Lys Leu Asp Asp Asp Leu Glu His
                 85              90                  95

Gln Gly Gly His Val Leu Asp His Gly His Lys His Lys His Gly His
                100             105             110

Gly His Gly Lys His Lys Asn Lys Gly Lys Lys Asn Gly Lys His Asn
            115             120             125

Gly Trp Lys Thr Glu His Leu Ala Ser Ser Ser Glu Asp Ser Thr Thr
     130             135             140

Pro Ser Ala Gln Thr Gln Glu Lys Thr Glu Gly Pro Thr Pro Ile Pro
145             150             155             160

Ser Leu Ala Lys Pro Gly Val Thr Val Thr Phe Ser Asp Phe Gln Asp
                165             170             175

Ser Asp Leu Ile Ala Thr Met Met Pro Pro Ile Ser Pro Ala Pro Ile
            180             185             190

Gln Ser Asp Asp Asp Trp Ile Pro Asp Ile Gln Ile Asp Pro Asn Gly
        195             200             205

Leu Ser Phe Asn Pro Ile Ser Asp Phe Pro Asp Thr Thr Ser Pro Lys
    210             215             220

Cys Pro Gly Arg Pro Trp Lys Ser Val Ser Glu Ile Asn Pro Thr Thr
225             230             235             240

Gln Met Lys Glu Ser Tyr Tyr Phe Asp Leu Thr Asp Gly Leu Ser
                245             250             255
```

DIAGNOSIS AND TREATMENT OF AUTOIMMUNE DISEASES

CROSS-REFERENCE TO RELATED APPLICATIONS

This application is a divisional application of U.S. application Ser. No. 15/030,790, filed on Apr. 20, 2016, now U.S. Pat. No. 10,101,344, which is a national stage filing under 35 U.S.C. § 371 of international PCT application PCT/US2014/061242, filed on Oct. 17, 2014, which claims priority to U.S. Provisional Application Ser. No. 61/893,542, filed on Oct. 21, 2013, the entire contents of each of which are incorporated by reference herein.

BACKGROUND

Plasma kallikrein (pKal) is the primary bradykinin-generating enzyme in the circulation and a component of the plasma kallikrein-kinin system (KKS). Colman, R. W., and Schmaier, A. H. (1997) *Blood* 90, 3819-3843. The activation of pKal occurs via the contact system which has been demonstrated to be causative in the disease pathology associated with hereditary angioedema (HAE). Zuraw, B. L., and Christiansen, S. C. (2008) *Expert Opin Investig Drugs* 17, 697-706. Bradykinin is a key mediator of pain, inflammation, edema and angiogenesis. Maurer, M., et al. (2011) *Allergy* 66, 1397-1406; Colman, R. W. (2006) *Curr Pharm Des* 12, 2599-2607.

SUMMARY

The present disclosure is based on the observations that the levels of cleaved high molecular weight kininogen (HMWK) are elevated in patients having an autoimmune disease, such as rheumatoid arthritis (RA), Crohn's disease (CD), and ulcerative colitis (UC). Accordingly, disclosed herein are methods for diagnosing an autoimmune disease such as RA, CD or UC, monitoring progress of the autoimmune disease, or assessing efficacy of a treatment for the autoimmune disease based on the level of cleaved HMWK.

In one aspect, the present disclosure provides a method of diagnosing an autoimmune disease (e.g., RA, CD, or UC) in a subject, the method comprising: (i) providing a biological sample (e.g., a serum sample or a plasma sample) of a subject suspected of having the autoimmune disease; (ii) measuring a level of cleaved high molecular weight kininogen (HMWK) in the biological sample; and (iii) identifying the subject as having or at risk for the autoimmune disease, if the level of cleaved HMWK in the biosample is elevated as compared to a control sample.

In some embodiments, the level of cleaved HMWK is measured by an assay that involves a binding agent (e.g., an antibody) specific to cleaved HMWK. The assay can be an enzyme-linked immunosorbent assay (ELISA) or an immunoblotting assay, e.g., a Westernblotting assay involving LiCor detection.

The method can further comprise subjecting the subject to a treatment for the autoimmune disease. In some embodiments, the subject is administered with an effective amount of a plasma kallikrein (pKal) inhibitor, e.g., those described herein.

In another aspect, the present disclosure provides a method of monitoring development of an autoimmune disease (e.g., RA, CD, or UC) in a subject, the method comprising: (i) providing a first biological sample of a subject suspected of having the autoimmune disease at a first time point; (ii) measuring a first level of high molecular weight kininogen (HMWK) in the first biological sample; (iii) providing a second biological sample of the subject at a second time point subsequent to the first time point; (iv) measuring a second level of cleaved HMWK in the second biological sample; and (v) assessing development of the autoimmune disease in the subject based on the change of the levels of cleaved HMWK in the first and second biological samples. If the second level of cleaved HMWK is higher than the first level of cleaved HMWK, it indicates that the autoimmune disease progresses in the subject or the subject has developed or is at risk for developing the autoimmune disease.

In some embodiments, the first biological sample, the second biological sample, or both are serum samples or plasma samples. In other embodiments, the first or second level of cleaved HMWK is measured by an assay that involves a binding agent (e.g., an antibody) specific to cleaved HMWK. In some examples, the assay is an enzyme-linked immunosorbent assay (ELISA) or an immunoblotting assay, e.g., a Westernblotting assay involving LiCor detection.

The method may further comprise subjecting the subject to a treatment for the autoimmune disease. In some embodiments, the subject is administered with an effective amount of a plasma kallikrein (pKal) inhibitor such as those described herein.

Further, the present disclosure provides a method of assessing the efficacy of a treatment for an autoimmune disease (e.g., RA, CD, or UC) in a patient, the method comprising: (i) providing multiple biological samples (e.g., serum samples or plasma samples) of a patient subjected to a treatment for an autoimmune disease during the course of the treatment; (ii) measuring the levels of high molecular weight kininogen (HMWK) in the multiple biological samples; and (iii) assessing the efficacy of the treatment in the patient based on the change of the levels of cleaved HMWK over the course of the treatment. If the level of cleaved HMWK decreases during the course of the treatment, it indicates that the treatment is effective in the patient.

In some embodiments, the treatment involves at least one plasma kallikrein inhibitor, e.g., those described herein. In other embodiments, the levels of cleaved HMWK in the multiple biological samples are measured by an assay that involves a binding agent (e.g., an antibody) specific to cleaved HMWK. In some examples, the assay is an enzyme-linked immunosorbent assay (ELISA) or an immunoblotting assay, e.g., a Western blotting assay involving LiCor detection. In any of the methods described herein, the biological sample used therein may comprise a protease inhibitor or a protease inhibitor cocktail, which is added to the biological sample after collection.

The kallikrein inhibitor useful in the methods may be, e.g., a plasma kallikrein (pKal) inhibitor. In some embodiments, the inhibitor is a plasma kallikrein inhibitor.

The kallikrein inhibitors useful in the methods may be any of the Kunitz domain polypeptides known in the art or described herein, larger polypeptides comprising any such Kunitz domains, provided the kallikrein inhibitor polypeptides bind and inhibit kallikrein as determined in standard assays, kallikrein binding proteins (e.g., antibodies, e.g., anti-plasma kallikrein antibodies), or other kallikrein inhibitors described herein.

Exemplary Kunitz domain peptides capable of inhibiting pKal activity includes: Glu Ala Met His Ser Phe Cys Ala Phe Lys Ala Asp Asp Gly Pro Cys Arg Ala Ala His Pro Arg Trp Phe Phe Asn Ile Phe Thr Arg Gln Cys Glu Glu Phe Ile Tyr Gly Gly Cys Glu Gly Asn Gln Asn Arg Phe Glu Ser Leu Glu Glu Cys Lys Lys Met Cys Thr Arg Asp (SEQ ID NO:2; DX-88), or a fragment thereof, such as amino acids 3-60 of SEQ ID NO:2.

In some embodiments, the kallikrein inhibitor comprises or consists of a framework region of a kunitz domain and first and second binding loop regions of the DX-88 polypeptide.

In some embodiments, the kallikrein inhibitor comprises or consists of an about 58-amino acid sequence of amino acids 3-60 of SEQ ID NO:2 or the DX-88 polypeptide having the 60-amino acid sequence of SEQ ID NO:2.

In some embodiments, the kallikrein inhibitor comprises a plasma kallikrein binding protein (e.g., antibody, e.g., an anti-plasma kallikrein antibody described herein).

In some embodiments, the binding protein (e.g., antibody, e.g., human antibody) binds the same epitope or competes for binding with a protein described herein.

In some embodiments, the protein described herein is selected from the group consisting of M162-A04, M160-G12, M142-H08, X63-G06, X101-A01 (also referred to herein as DX-2922), X81-B01, X67-D03, X67-G04, X81-B01, X67-D03, X67-G04, X115-B07, X115-D05, X115-E09, X115-H06, X115-A03, X115-01, X115-F02, X124-G01 (also referred to herein as DX-2930), X115-G04, M29-D09, M145-D11, M06-D09 and M35-G04. Such binding proteins are described, e.g., in PCT Publication WO2012/094587 and US Patent Application Publication US 20100183625, both of which are incorporated herein by reference in their entirety.

In some embodiments, the plasma kallikrein binding protein competes with or binds the same epitope as X81-B01, X67-D03, X101-A01, M162-A04, X115-F02, X124-G01, or X63-G06.

In some embodiments, the plasma kallikrein binding protein does not bind prekallikrein (e.g., human prekallikrein), but binds to the active form of plasma kallikrein (e.g., human plasma kallikrein).

In certain embodiments, the protein binds at or near the active site of the catalytic domain of plasma kallikrein, or a fragment thereof, or binds an epitope that overlaps with the active site of plasma kallikrein.

In some embodiments, the protein binds to one or more amino acids that form the catalytic triad of plasma kallikrein: His434, Asp483, and/or Ser578 (numbering based on the human sequence). In other embodiments, the protein binds to one or more amino acids of Ser479, Tyr563, and/or Asp585 (numbering based on the human sequence). In yet other embodiments, the plasma kallikrein binding protein binds one or more amino acids of: Arg 551, Gln 553, Tyr 555, and/or Arg 560 (amino acid position numbering based on the human kallikrein sequence). In still other embodiments, the plasma kallikrein binding protein binds one or more amino acids of: Ser 478, Asn 481. Ser 525, and/or Lys 526 (amino acid position numbering based on the human kallikrein sequence).

In some embodiments, the plasma kallikrein binding protein decreases Factor XIIa and/or bradykinin production by greater than about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95% as compared to a standard, e.g., the Factor XIIa and/or bradykinin production under the same conditions but in the absence of the protein.

In some embodiments, the plasma kallikrein binding protein has an apparent inhibition constant ($K_{i,app}$) of less than 1000, 500, 100, or 10 nM.

In one embodiment, the HC and LC variable domain sequences are components of the same polypeptide chain.

In another embodiment, the HC and LC variable domain sequences are components of different polypeptide chains. For example, the plasma kallikrein binding protein is an IgG, e.g., IgG1, IgG2, IgG3, or IgG4. The plasma kallikrein binding protein can be a soluble Fab (sFab).

In other implementations the plasma kallikrein binding protein includes a Fab2', scFv, minibody, scFv::Fc fusion, Fah::HSA fusion, HSA::Fah fusion, Fab::HSA::Fah fusion, or other molecule that comprises the antigen combining site of one of the binding proteins herein. The VH and VL regions of these Fabs can be provided as IgG Fab. Fab2, Fab2', scFv. PEGylated Fab, PEGylated scFv, PEGylated Fab2, VH::CH1::HSA+LC, HSA::VH::CH1+LC, LC::HSA+VH::CH1, HSA::LC+VH::CH1, or other appropriate construction.

In one embodiment, the plasma kallikrein binding protein is a human or humanized antibody or is non-immunogenic in a human. For example, the protein includes one or more human antibody framework regions, e.g., all human framework regions.

In one embodiment, the plasma kallikrein binding protein includes a human Fc domain, or an Fc domain that is at least 95, 96, 97, 98, or 99% identical to a human Fc domain.

In one embodiment, the plasma kallikrein binding protein is a primate or primatized antibody or is non-immunogenic in a human. For example, the protein includes one or more primate antibody framework regions, e.g., all primate framework regions.

In one embodiment, the plasma kallikrein binding protein includes a primate Fc domain, or an Fc domain that is at least 95, 96, 97, 98, or 99% identical to a primate Fc domain. "Primate" includes humans (*Homo sapiens*), chimpanzees (*Pan troglodytes* and *Pan paniscus* (bonobos)), gorillas (*Gorilla gorilla*), gibons, monkeys, lemurs, aye-ayes (*Daubentonia madagascariensis*), and tarsiers.

In one embodiment, the plasma kallikrein binding protein includes human framework regions, or framework regions that are at least 95, 96, 97, 98, or 99% identical to human framework regions.

In certain embodiments, the plasma kallikrein binding protein includes no sequences from mice or rabbits (e.g., is not a murine or rabbit antibody).

In some embodiments, the binding protein (e.g., antibody such as human antibody) comprises a heavy chain immunoglobulin variable domain sequence and a light chain immunoglobulin variable domain sequence, wherein: the heavy chain immunoglobulin variable domain sequence comprises one, two, or three (e.g., three) CDR regions from the heavy chain variable domain of a protein described herein, and/or the light chain immunoglobulin variable domain sequence comprises one, two, or three (e.g., three) CDR regions from the light chain variable domain of a protein described herein, wherein the protein binds to (e.g., and inhibits) plasma kallikrein.

In some embodiments, the heavy chain immunoglobulin variable domain sequence comprises one, two, or three (e.g., three) CDR regions from the heavy chain variable domain of M162-A04, M160-G12, M142-H08, X63-G06, X101-A01 (also referred to herein as DX-2922), X81-B01, X67-D03, X67-G04, X81-B01, X67-D03, X67-G04, X115-B07, X115-D05, X115-E09, X115-H06, X115-A03, X115-D01, X115-F02, X124-G01 (also referred to herein as DX-2930), X115-G04, M29-D09, M145-D11, M06-D09 and M35-G04, and/or the light chain immunoglobulin variable domain sequence comprises one, two, or three (e.g., three) CDR regions from the light chain variable domain of M162-A04, M160-G12, M142-H08, X63-G06, X101-A01 (also referred to herein as DX-2922), X81-B01, X67-D03, X67-G04, X81-B01, X67-D03, X67-G04, X115-B07, X115-D05, X115-E09, X115-H06, X115-A03, X115-D01, X115-F02, X124-G01 (also referred to herein as DX-2930), X115-G04, M29-D09, M145-D11, M06-D09 and M35-G4304 (respectively).

In some embodiments, the one, two, or three (e.g., three) CDR regions from the heavy chain variable domain are from X81-B01 and/or the one, two, or three (e.g., three) CDR regions from the light chain variable domain are from X81-B01 or from X67-D03.

In some embodiments, the heavy chain immunoglobulin variable domain sequence comprises the heavy chain variable domain of a protein described herein, and/or the light chain immunoglobulin variable domain sequence comprises the light chain variable domain of a protein described herein.

In some embodiments, the heavy chain immunoglobulin variable domain sequence comprises the heavy chain variable domain of M162-A04, M160-G12, M142-H08, X63-G06, X101-A01 (also referred to herein as DX-2922), X81-B01, X67-D03, X67-G04, X81-B01, X67-D03, X67-G04, X115-807, X115-D05, X115-E09, X115-H06, X115-A03, X115-D01, X115-F02, X124-G01 (also referred to herein as DX-2930), X115-G04, M29-D09, M145-D11, M06-D09 and M35-G04, and/or the light chain immunoglobulin variable domain sequence comprises the light chain variable domain of M162-A04, M160-G12, M142-H08, X63-G06, X101-A01 (also referred to herein as DX-2922), X81-B01, X67-D03, X67-G04, X81-B01, X67-D03, X67-G04, X115-B07, X115-D05, X115-E09, X115-H06, X115-A03, X115-D01, X115-F02, X124-001 (also referred to herein as DX-2930), X115-004, M29-D09, M145-D11, M06-D09 and M35-G04 (respectively).

In some embodiments, the heavy chain immunoglobulin variable domain sequence comprises the heavy chain variable domain of X81-B01, and/or the light chain immunoglobulin variable domain sequence comprises the light chain variable domain of X81-B01.

In some embodiments, the heavy chain immunoglobulin variable domain sequence comprises the heavy chain variable domain of X67-D03, X101-A01, M162-A04, X115-F02, X124-G01, or X63-G06 and/or the light chain immunoglobulin variable domain sequence comprises the light chain variable domain of X67-D03, X101-A01, M162-A04, X115-F02, X124-G01, or X63-G06 (respectively).

In some embodiments, the protein comprises the heavy chain of a protein described herein, and/or the light chain of a protein described herein.

In some embodiments, the protein comprises the heavy chain of M162-A04, M160-G12, M142-H08, X63-G06, X101-A01 (also referred to herein as DX-2922), X81-B01, X67-D03, X67-G04, X81-B01, X67-D03, X67-G04, X115-B07, X115-D05, X115-E09, X115-1106, X115-A03, X115-D01, X115-F02, X124-G01 (also referred to herein as DX-2930), X115-G04, M29-D09, M145-D11, M06-D09 and M35-G04 (respectively).

In some embodiments, the protein comprises the heavy chain of X81-B01, and/or the light chain of X81-B01.

In some embodiments, the protein comprises the heavy chain of X67-D03, X101-A01, M162-A04, X115-F02, X124-G01, or X63-G06 and/or the light chain of X67-D03, X101-A01, M162-A04, X115-F02, X124-G01, or X63-G06 (respectively).

In some embodiments, the protein includes one or more of the following characteristics: (a) a human CDR or human framework region; (b) the HC immunoglobulin variable domain sequence comprises one or more (e.g., 1, 2, or 3) CDRs that are at least 85, 88, 89, 90, 91, 92, 93, 94, 95, 96, 97, 98, 99, or 100% identical to a CDR of a HC variable domain described herein; (c) the LC immunoglobulin variable domain sequence comprises one or more (e.g., 1, 2, or 3) CDRs that are at least 85, 88, 89, 90, 91, 92, 93, 94, 95, 96, 97, 98, 99, or 100% identical to a CDR of a LC variable domain described herein; (d) the LC immunoglobulin variable domain sequence is at least 85, 88, 89, 90, 91, 92, 93, 94, 95, 96, 97, 98, 99, or 100% identical to a LC variable domain described herein (e.g., overall or in framework regions or CDRs); (e) the HC immunoglobulin variable domain sequence is at least 85, 88, 89, 90, 91, 92, 93, 94, 95, 96, 97, 98, 99, or 100% identical to a HC variable domain described herein (e.g., overall or in framework regions or CDRs); (f) the protein binds an epitope bound by a protein described herein, or competes for binding with a protein described herein; (g) a primate CDR or primate framework region; (h) the HC immunoglobulin variable domain sequence comprises a CDR1 that differs by at least one amino acid but by no more than 2 or 3 amino acids from the CDR1 of a HC variable domain described herein; (i) the HC immunoglobulin variable domain sequence comprises a CDR2 that differs by at least one amino acid but by no more than 2, 3, 4, 5, 6, 7, or 8 amino acids from the CDR2 of a HC variable domain described herein; (j) the HC immunoglobulin variable domain sequence comprises a CDR3 that differs by at least one amino acid but by no more than 2, 3, 4, 5, or 6 amino acids from the CDR3 of a HC variable domain described herein; (k) the LC immunoglobulin variable domain sequence comprises a CDR1 that differs by at least one amino acid but by no more than 2, 3, 4, or 5 amino acids from the CDR1 of a LC variable domain described herein; (l) the LC immunoglobulin variable domain sequence comprises a CDR2 that differs by at least one amino acid but by no more than 2, 3, or 4 amino acids from the CDR2 of a LC variable domain described herein; (m) the LC immunoglobulin variable domain sequence comprises a CDR3 that differs by at least one amino acid but by no more than 2, 3, 4, or 5 amino acids from the CDR3 of a LC variable domain described herein; (n) the LC immunoglobulin variable domain sequence differs by at least one amino acid but by no more than 2, 3, 4, 5, 6, 7, 8, 9, or 10 amino acids from a LC variable domain described herein (e.g., overall or in framework regions or CDRs); and (o) the HC immunoglobulin variable domain sequence differs by at least one amino acid but by no more than 2, 3, 4, 5, 6, 7, 8, 9, or 10 amino acids from a HC variable domain described herein (e.g., overall or in framework regions or CDRs).

In some embodiments, the protein has an apparent inhibition constant ($K_{i,app}$) of less than 1000, 500, 100, or 10 nM.

In a preferred embodiment, the protein is an antibody (e.g., a human antibody) having the light and heavy chains of antibodies selected from the group consisting of M162-A04, M160-G12, M142-H08, X63-G06, X101-A01 (also referred to herein as DX-2922), X81-B01, X67-D03, X67-G04, X81-B01, X67-D03, X67-G04, X115-B07, X115-D05, X115-E09, X115-H06, X115-A03, X115-D01, X115-F02, X124-G01 (also referred to herein as DX-2930), X115-G04, M29-D09, M145-D11, M06-D09 and M35-G04.

In a preferred embodiment, the protein is an antibody (e.g., a human antibody) having the heavy chain of an antibody selected from the group consisting of: M162-A04, M160-G12, M142-H08, X63-G06, X101-A01 (also referred to herein as DX-2922), X81-B01, X67-D03, X67-G04, X81-B01, X67-D03, X67-G04, X115-B07, X115-D05, X115-E09, X115-H06, X115-A03, X115-D01, X115-F02, X124-G01 (also referred to herein as DX-2930), X115-G04, M29-D09, M145-D11, M06-D09 and M35-G04.

In a preferred embodiment, the protein is an antibody (e.g., a human antibody) having the light chain of an antibody selected from the group consisting of: M162-A04, M160-G12, M142-1108, X63-06, X101-A01 (also referred to herein as DX-2922), X81-B01, X67-D03, X67-G04, X81-BO 1, X67-D03, X67-G04, X115-B07, X115-D05, X115-E09, X115-H06, X115-A03, X115-D01, X115-F02, X124-G01 (also referred to herein as DX-2930), X115-G04, M29-D09, M145-D11, M06-D09 and M35-G04.

In a preferred embodiment, the protein is an antibody (e.g., a human antibody) having light and/or heavy antibody variable regions of an antibody selected from the group consisting of M162-A04, M160-G12, M142-H08, X63-G06, X101-A01 (also referred to herein as DX-2922), X81-B01, X67-D03, X67-G04, X81-B01, X67-D03, X67-G04, X115-B07, X115-D05, X115-E09, X115-1106, X1115-A03, X115-D01, X115-F02, X124-G01 (also referred to herein as DX-2930), X115-004, M29-D09, M145-D11, M06-D09 and M35-G04.

In some embodiments, the plasma kallikrein binding protein does not bind prekallikrein (e.g., human prekallikrein), but binds to the active form of plasma kallikrein (e.g., human plasma kallikrein).

In some embodiments, the plasma kallikrein binding protein decreases Factor XIIa and/or bradykinin production by greater than about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95% as compared to a standard, e.g., the Factor XIIa and/or bradykinin production under the same conditions but in the absence of the protein.

In some embodiments, the plasma kallikrein binding protein has an apparent inhibition constant ($K_{i,app}$) of less than 1000, 500, 100, or 10 nM.

In one embodiment, the HC and LC variable domain sequences are components of the same polypeptide chain.

The details of one or more embodiments of the present disclosure present disclosure are set forth in the accompanying drawings and the description below. Other features, objects, and advantages of the present disclosure will be apparent from the description and drawings, and from the claims.

The contents of all references, pending patent applications and published patents, cited throughout this application are hereby expressly incorporated by reference.

BRIEF DESCRIPTION OF THE FIGURES

FIG. 1 is a chart showing the association of cleaved HMWK with rheumatoid arthritis, Crohn's disease, and ulcerative colitis.

DETAILED DESCRIPTION

The present disclosure is based on the unexpected discovery that elevated levels of cleaved HMWK were observed in patients having RA, CD, or UC. In particular, an extensive level of cleaved HMWK was observed in RA patients and a moderate level of cleaved HMWK was observed in both CD and UC patients. Accordingly, provided herein are new diagnostic and prognostic methods for identifying subjects having or at risk for developing an autoimmune disease such as RA. UC, or CD, monitoring progress of the autoimmune disease, and assessing the efficacy of a treatment for the autoimmune disease in a subject based on the level of cleaved HMWK in a biological sample of the subject. Also described herein are methods for treating such an autoimmune disease, as well as other diseases associated with the plasma kallikrein (pKal) system using a pKal inhibitor such as those described herein.

Definitions

For convenience, before further description of the present disclosure, certain terms employed in the specification, examples and appended claims are defined here.

The singular forms "a", "an", and "the" include plural references unless the context clearly dictates otherwise.

The term "antibody" refers to a protein that includes at least one immunoglobulin variable domain or immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses antigen-binding fragments of antibodies (e.g., single chain antibodies. Fab and sFab fragments, F(ab')$_2$, Fd fragments. Fv fragments, scFv, and domain antibodies (dAb) fragments (de Wildt et al., Eur J Immunol. 1996; 26(3):629-39)) as well as complete antibodies. An antibody can have the structural features of IgA, IgG, IgE, IgD, IgM (as well as subtypes thereof). Antibodies may be from any source, but primate (human and non-human primate) and primatized are preferred.

The VH and VL regions can be further subdivided into regions of hypervariability, termed "complementarity determining regions" ("CDR"), interspersed with regions that are more conserved, termed "framework regions" ("FR"). The extent of the framework region and CDRs has been precisely defined (see. Kabat, E. A., et al. (1991) *Sequences of Proteins of Immunological Interest*, Fifth Edition, U.S. Department of Health and Human Services, NIH Publication No. 91-3242, and Chothia, C. et al. (1987) J. Mol. Biol. 196:901-917, see also www.hgmp.mrc.ac.uk). Kabat definitions are used herein. Each VH and VL is typically composed of three CDRs and four FRs, arranged from amino-terminus to carboxy-terminus in the following order: FR1, CDR1, FR2, CDR2, FR3, CDR3, FR4.

The VH or VL chain of the antibody can further include all or part of a heavy or light chain constant region, to thereby form a heavy or light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. In IgGs, the heavy chain constant region includes three immunoglobulin domains, CH1, CH2 and CH3. The light chain constant region includes a CL domain. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system. The light chains of the immunoglobulin may be of types kappa or lambda. In one embodiment, the antibody is glycosylated. An antibody can be functional for antibody-dependent cytotoxicity and/or complement-mediated cytotoxicity.

One or more regions of an antibody can be human or effectively human. For example, one or more of the variable regions can be human or effectively human. For example, one or more of the CDRs can be human, e.g., HC CDR1 HC CDR2, HC CDR3, LC CDR1. LC CDR2, and LC CDR3. Each of the light chain CDRs can be human. HC CDR3 can be human. One or more of the framework regions can be human, e.g., FR1, FR2, FR3, and FR4 of the HC or LC. For example, the Fc region can be human. In one embodiment, all the framework regions are human, e.g., have a sequence of a framework of an antibody produced by a human somatic cell, e.g., a hematopoietic cell that produces immunoglobulins or a non-hematopoietic cell. In one embodiment, the human sequences are germline sequences, e.g., encoded by a germline nucleic acid. In one embodiment, the framework (FR) residues of a selected Fab can be converted to the amino-acid type of the corresponding residue in the most similar primate germline gene, especially the human germline gene. One or more of the constant regions can be human or effectively human. For example, at least 70, 75, 80, 85, 90, 92, 95, 98, or 100% of an immunoglobulin variable domain, the constant region, the constant domains (CH1, CH2, CH3, CL1), or the entire antibody can be human or effectively human.

All or part of an antibody can be encoded by an immunoglobulin gene or a segment thereof. Exemplary human immunoglobulin genes include the kappa, lambda, alpha (IgA1 and TgA2), gamma (IgG1, IgG2, IgG3, IgG4), delta, epsilon and mu constant region genes, as well as the many immunoglobulin variable region genes. Full-length immunoglobulin "light chains" (about 25 KDa or about 214 amino acids) are encoded by a variable region gene at the NH2-terminus (about 110 amino acids) and a kappa or lambda constant region gene at the COOH-terminus. Full-length immunoglobulin "heavy chains" (about 50 KDa or about 446 amino acids), are similarly encoded by a variable region gene (about 116 amino acids) and one of the other aforementioned constant region genes, e.g., gamma (encoding about 330 amino acids). The length of human HC varies considerably because HC CDR3 varies from about 3 amino-acid residues to over 35 amino-acid residues.

The term "antigen-binding fragment" of a full length antibody refers to one or more fragments of a full-length antibody that retain the ability to specifically bind to a target of interest. Examples of binding fragments encompassed within the term "antigen-binding fragment" of a full length antibody include (i) a Fab fragment, a monovalent fragment consisting of the VL, VH, CL and CH1 domains; (ii) a F(ab')2 fragment, a bivalent fragment including two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR) that retains functionality. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules known as single chain Fv (scFv). See e.g., U.S. Pat. Nos. 5,260,203, 4,946,778, and 4,881,175; Bird et al. (1988) Science 242: 423-426; and Huston et al. (1988) *Proc. Natl. Acad. Sci. USA* 85:5879-5883.

Antibody fragments can be obtained using any appropriate technique including conventional techniques known to those with skill in the art. The term "monospecific antibody" refers to an antibody that displays a single binding specificity and affinity for a particular target, e.g., epitope. This term includes a "monoclonal antibody" or "monoclonal antibody composition." which as used herein refer to a preparation of antibodies or fragments thereof of single molecular composition, irrespective of how the antibody was generated.

The inhibition constant (Ki) provides a measure of inhibitor potency; it is the concentration of inhibitor required to reduce enzyme activity by half and is not dependent on enzyme or substrate concentrations. The apparent Ki ($K_{i,app}$) is obtained at different substrate concentrations by measuring the inhibitory effect of different concentrations of inhibitor (e.g., inhibitory binding protein) on the extent of the reaction (e.g., enzyme activity); fitting the change in pseudo-first order rate constant as a function of inhibitor concentration to the Morrison equation (Equation 1) yields an estimate of the apparent Ki value. The Ki is obtained from the y-intercept extracted from a linear regression analysis of a plot of Ki,app versus substrate concentration.

$$v = v_o - v_o \left( \frac{(K_{i,app} + I + E) - \sqrt{(K_{i,app} + I + E)^2 - 4 \cdot I \cdot E}}{2 \cdot E} \right) \quad \text{Equation 1}$$

Where v=measured velocity; $v_0$=velocity in the absence of inhibitor; $K_{i,app}$=apparent inhibition constant; I=total inhibitor concentration; and E=total enzyme concentration.

As used herein. "binding affinity" refers to the apparent association constant or $K_a$. The $K_a$ is the reciprocal of the dissociation constant ($K_d$). A binding protein may, for example, have a binding affinity of at least $10^5$, $10^6$, $10^7$, $10^8$, $10^9$, $10^{10}$ and $10^{11}$ $M^{-1}$ for a particular target molecule. Higher affinity binding of a binding protein to a first target relative to a second target can be indicated by a higher $K_a$ (or a smaller numerical value $K_d$) for binding the first target than the $K_a$ (or numerical value $K_d$) for binding the second target. In such cases, the binding protein has specificity for the first target (e.g., a protein in a first conformation or mimic thereof) relative to the second target (e.g., the same protein in a second conformation or mimic thereof; or a second protein). Differences in binding affinity (e.g., for specificity or other comparisons) can be at least 1.5, 2, 3, 4, 5, 10, 15, 20, 37.5, 50, 70, 80, 91, 100, 500, 1000, or $10^5$ fold.

Binding affinity can be determined by a variety of methods including equilibrium dialysis, equilibrium binding, gel filtration, ELISA, surface plasmon resonance, or spectroscopy (e.g., using a fluorescence assay). Exemplary conditions for evaluating binding affinity are in TRIS-buffer (50 mM TRIS, 150 mM NaCl, 5 mM $CaCl_2$ at pH7.5). These techniques can be used to measure the concentration of bound and free binding protein as a function of binding protein (or target) concentration. The concentration of bound binding protein ([Bound]) is related to the concentration of free binding protein ([Free]) and the concentration of binding sites for the binding protein on the target where (N) is the number of binding sites per target molecule by the following equation:

[Bound]=$N \cdot$[Free]/((1/$K_a$)+[Free]).

It is not always necessary to make an exact determination of $K_a$, though, since sometimes it is sufficient to obtain a quantitative measurement of affinity, e.g., determined using a method such as ELISA or FACS analysis, is proportional to $K_a$, and thus can be used for comparisons, such as determining whether a higher affinity is, e.g., 2-fold higher, to obtain a qualitative measurement of affinity, or to obtain an inference of affinity, e.g., by activity in a functional assay, e.g., an in vitro or in vivo assay.

The term "binding protein" refers to a protein that can interact with a target molecule. This term is used interchangeably with "ligand." A "plasma kallikrein binding protein" refers to a protein that can interact with (e.g., bind) plasma kallikrein, and includes, in particular, proteins that preferentially or specifically interact with and/or inhibit plasma kallikrein. A protein inhibits plasma kallikrein if it causes a decrease in the activity of plasma kallikrein as compared to the activity of plasma kallikrein in the absence of the protein and under the same conditions. In some embodiments, the plasma kallikrein binding protein is an antibody.

The term "kallikrein inhibitor" refers to any agent or molecule that inhibits kallikrein.

The term "combination" refers to the use of the two or more agents or therapies to treat the same patient, wherein the use or action of the agents or therapies overlap in time. The agents or therapies can be administered at the same time (e.g., as a single formulation that is administered to a patient or as two separate formulations administered concurrently) or sequentially in any order.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

It is possible for one or more framework and/or CDR amino acid residues (or binding loop amino acid residues) of a binding protein to include one or more mutations (e.g., substitutions (e.g., conservative substitutions or substitutions of non-essential amino acids), insertions, or deletions) relative to a binding protein described herein. A plasma kallikrein binding protein may have mutations (e.g., substitutions (e.g., conservative substitutions or substitutions of non-essential amino acids), insertions, or deletions) (e.g., at least one, two, three, or four, and/or less than 15, 12, 10, 9, 8, 7, 6, 5, 4, 3, or 2 mutations) relative to a binding protein described herein, e.g., mutations which do not have a substantial effect on protein function. The mutations can be present in framework regions, CDRs (or binding loops), and/or constant regions. In some embodiments, the mutations are present in a framework region. In some embodiments, the mutations are present in a CDR. In some embodiments, the mutations are present in a constant region. Whether or not a particular substitution will be tolerated, i.e., will not adversely affect biological properties, such as binding activity can be predicted, e.g., by evaluating whether the mutation is conservative or by the method of Bowie, et al. (1990) Science 247:1306-1310.

An "effectively human" immunoglobulin variable region is an immunoglobulin variable region that includes a sufficient number of human framework amino acid positions such that the immunoglobulin variable region does not elicit an immunogenic response in a normal human. An "effectively human" antibody is an antibody that includes a sufficient number of human amino acid positions such that the antibody does not elicit an immunogenic response in a normal human.

An "epitope" refers to the site on a target compound that is bound by a binding protein (e.g., an antibody such as a Fab or full length antibody). In the case where the target compound is a protein, the site can be entirely composed of amino acid components, entirely composed of chemical modifications of amino acids of the protein (e.g., glycosyl moieties), or composed of combinations thereof. Overlapping epitopes include at least one common amino acid residue, glycosyl group, phosphate group, sulfate group, or other molecular feature.

A first binding protein (e.g., antibody) "binds to the same epitope" as a second binding protein (e.g., antibody) if the first binding protein binds to the same site on a target compound that the second binding protein binds, or binds to a site that overlaps (e.g., 50%, 60%, 70%, 80%, 90%, or 100% overlap, e.g., in terms of amino acid sequence or other molecular feature (e.g., glycosyl group, phosphate group, or sulfate group)) with the site that the second binding protein binds.

A first binding protein (e.g., antibody) "competes for binding" with a second binding protein (e.g., antibody) if the binding of the first binding protein to its epitope decreases (e.g., by 10%, 20%, 30%, 40%, 50%, 60%, 70%, 80%, 90%, 100%, or more) the amount of the second binding protein that binds to its epitope. The competition can be direct (e.g., the first binding protein binds to an epitope that is the same as, or overlaps with, the epitope bound by the second binding protein), or indirect (e.g., the binding of the first binding protein to its epitope causes a steric change in the target compound that decreases the ability of the second binding protein to bind to its epitope).

Calculations of "homology" or "sequence identity" between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The optimal alignment is determined as the best score using the GAP program in the GCG software package with a Blossum 62 scoring matrix with a gap penalty of 12, a gap extend penalty of 4, and a frameshift gap penalty of 5. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences.

In a preferred embodiment, the length of a reference sequence aligned for comparison purposes is at least 30%, preferably at least 40%, more preferably at least 50%, even more preferably at least 60%, and even more preferably at least 70%, 80%, 90%, 92%, 95%, 97%, 98%, or 100% of the length of the reference sequence. For example, the reference sequence may be the length of the immunoglobulin variable domain sequence.

A "humanized" immunoglobulin variable region is an immunoglobulin variable region that is modified to include a sufficient number of human framework amino acid positions such that the immunoglobulin variable region does not elicit an immunogenic response in a normal human. Descriptions of "humanized" immunoglobulins include, for example, U.S. Pat. Nos. 6,407,213 and 5,693,762.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons. N.Y. (1989), 6.3.1-6.3.6. Aqueous and nonaqueous methods are described in that reference and either can be used. Specific hybridization conditions referred to herein are as follows: (1) low stringency hybridization conditions in 6× sodium chloride/sodium citrate (SSC) at about 45° C. followed by two washes in 0.2×SSC, 0.1% SDS at least at 50° C. (the temperature of the washes can be increased to 55° C. for low stringency conditions); (2) medium stringency hybridization conditions in 6×SSC at about 45° C., followed by one or more washes in 0.2×SSC, 0.1% SDS at 60° C.; (3) high stringency hybridization conditions in 6×SSC at about 45° C., followed by one or more washes in 0.2×SSC, 0.1% SDS at 65° C.; and (4) very high stringency hybridization conditions are 0.5M sodium phosphate, 7% SDS at 65° C. followed by one or more washes at 0.2×SSC, 1% SDS at 65° C. Very high stringency conditions (4) are the preferred conditions and the ones that should be used unless otherwise specified. The disclosure includes nucleic acids that hybridize with low, medium, high, or very high stringency to a nucleic acid described herein or to a complement thereof, e.g., nucleic acids encoding a binding protein described herein. The nucleic acids can be the same length or within 30, 20, or 10% of the length of the reference nucleic acid. The nucleic acid can correspond to a region encoding an immunoglobulin variable domain sequence described herein.

An "isolated composition" refers to a composition that is removed from at least 90% of at least one component of a natural sample from which the isolated composition can be obtained. Compositions produced artificially or naturally can be "compositions of at least" a certain degree of purity if the species or population of species of interests is at least 5, 10, 25, 50, 75, 80, 90, 92, 95, 98, or 99% pure on a weight-weight basis.

An "isolated" protein refers to a protein that is removed from at least 90% of at least one component of a natural sample from which the isolated protein can be obtained. Proteins can be "of at least" a certain degree of purity if the species or population of species of interest is at least 5, 10, 25, 50, 75, 80, 90, 92, 95, 98, or 99% pure on a weight-weight basis.

A "non-essential" amino acid residue is a residue that can be altered from the wild-type sequence of the binding agent, e.g., the antibody, without abolishing or more preferably, without substantially altering a biological activity, whereas changing an "essential" amino acid residue results in a substantial loss of activity.

A "patient". "subject" or "host" (these terms are used interchangeably) to be treated by the method may mean either a human or non-human animal.

A "subject in need thereof" includes, for example, a subject having a disease or disorder described herein or a subject at risk for developing a disease or disorder described herein.

The term "kallikrein" (e.g., plasma kallikrein) refers to peptidases (enzymes that cleave peptide bonds in proteins), a subgroup of the serine protease family. Plasma kallikrein cleaves kininogen to generate kinins, potent pro-inflammatory peptides. DX-88 (also referred to herein as "PEP-1") is a potent (Ki<1 nM) and specific inhibitor of plasma kallikrein (NP_000883). (See also e.g., WO 95/21601 or WO 2003/103475).

The amino acid sequence of KLKb1 (plasma kallikrein) is:

```
KLKb1
>gi|78191798|ref|NP_000883.2| plasma kallikrein
B1 precursor [Homo sapiens]
                                         (SEQ ID NO: 3)
     MILFKQATYFISLFATVSCGCLTQLYENAFFRGGDVASMYTPNA

QYCQMRCTFHPRCLLFSFLPASSINDMEKRFGCFLKDSVTGTLPKVHRIG

AVSGHSLKQCGHQISACHRDIYKGVDMRGVNFNVSKVSSVEECQKRCTSN

IRCQFFSYATQTFHKAEYRNNCLLKYSPGGTPTAIKVLSNVESGFSLKPC

ALSEIGCHMNIFQHLAFSDVDVARVLTPDAFVCRTICTYHPNCLFFTFYT

NVWKIESQRNVCLLKTSESGTPSSSTPQENTISCYSLLTCKRTLPEPCHS

KIYPGVDFGGEELNVTFVKGVNVCQEICTKMIRCQFFTYSLLPEDCKEEK

CKCFLRLSMDGSPTRIAYGTQGSSGYSLRLCNTGDNSVCTTKTSTRIVGG

TNSSWGEWPWQVSLQVKLTAQRHLCGGSLIGHQWVLTAAHCFDGLPLQDV

WRIYSGILNLSDITKDIPFSOIKEIIIHQNYKVSEGNHDIALIKLQAPLN

YIEFQKPICLPSKGDISIIYINCWVIGWGFSKEKGEIQNILQKVNIPLVT

NEECQKRYQDYKITQRMVCAGYKEGGKDACKGDSGGPLVCKHNGMWRLVG

ITSWGEGCARREQPGVYTKVAEYMDWILEKTQSSDGKAQMQSPA.
```

As used herein the term "DX-2922" as used interchangeably with the term "X101-A01". Other variants of this antibody are described below.

| Antibody Identification | Description |
| --- | --- |
| X63-G06 | Non-germlined Fab discovered using ROLIC, same HC but different LC as M160-G12 |
| X81-B01 | Germlined IgG produced in HEK 293T cells |
| X101-A01 | Germlined IgG produced in CHO cells, same HC and LC sequence as X81-B01 |
| DX-2922 | Alternate nomenclature for X101-A01 |

As used herein the term "DX-2930" as used interchangeably with the term "X124-G01". Other variants of this antibody are described below.

| Antibody Identification | Description |
| --- | --- |
| M162-A04 | Non-germlined Fab discovered using phage display |
| M199-A08 | Heavy chain CDR3 varied Fab derived by affinity maturation of M162-A04 |
| X115-F02 | Germlined Fab produced in 293T cells, same variable heavy chain as X124-G01 |

-continued

| Antibody Identification | Description |
|---|---|
| X124-001 or DX-2930 | Germlined IgG produced in CHO cells, LC and HC sequence as X115-F02 except that the C-terminal Lys of the HC is removed in X124 -G01 (also known as DX-2930). |

KLK1

>gi|13529059|gb|AAH05313.1| Kallikrein 1
[Homo sapiens]
(SEQ ID NO: 4)
MWFLVLCLALSLGGTGAAPPIQSRIVGGWECEQHSQPWQAALYHFSTFQC

GGILVHRQWVLTAAHCISDNYQLWLGRHNLFDDENTAQFVHVSESFPHPG

FNMSLLENHTRQADEDYSHDLMLLRLTEPADTITDAVKVVELPTQEPEVG

STCLASGWGSIEPENFSFPDDLQCVDLKILPNDECKKVHVQKVTDFMLCV

GHLEGGKDTCVGDSGGPLMCDGVLQGVTSWGYVPCGTPNKPSVAVRVLSY

VKWIEDTIAENS

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

The term "preventing" a disease in a subject refers to subjecting the subject to a pharmaceutical treatment, e.g., the administration of a drug, such that at least one symptom of the disease is prevented, that is, administered prior to clinical manifestation of the unwanted condition (e.g., disease or other unwanted state of the host animal) so that it protects the host against developing the unwanted condition. "Preventing" a disease may also be referred to as "prophylaxis" or "prophylactic treatment."

A "prophylactically effective amount" refers to an amount effective, at dosages and for periods of time necessary, to achieve the desired prophylactic result. Typically, because a prophylactic dose is used in subjects prior to or at an earlier stage of disease, the prophylactically effective amount is likely but not necessarily less than the therapeutically effective amount.

As used herein, the term "substantially identical" (or "substantially homologous") is used herein to refer to a first amino acid or nucleic acid sequence that contains a sufficient number of identical or equivalent (e.g., with a similar side chain, e.g., conserved amino acid substitutions) amino acid residues or nucleotides to a second amino acid or nucleic acid sequence such that the first and second amino acid or nucleic acid sequences have (or encode proteins having) similar activities, e.g., a binding activity, a binding preference, or a biological activity. In the case of antibodies, the second antibody has the same specificity and has at least 50%, at least 25%, or at least 10% of the affinity relative to the same antigen.

Sequences similar or homologous (e.g., at least about 85% sequence identity) to the sequences disclosed herein are also part of this application. In some embodiments, the sequence identity can be about 85%, 90%, 91%, 92%, 93%, 94%, 95%, 96%, 97%, 98%, 99% or higher. In some embodiments, a plasma kallikrein binding protein can have about 85%, 90%, 91%, 92%, 93%, 94%, 95%, 96%, 97%, 98%, 99% or higher sequence identity to a binding protein described herein. In some embodiments, a plasma kallikrein binding protein can have about 85%, 90%, 91%, 92%, 93%, 94%, 95%, 96%, 97%, 98%, 99% or higher sequence identity in the HC and/or LC framework regions (e.g., HC and/or LC FR 1, 2, 3, and/or 4) to a binding protein described herein. In some embodiments, a plasma kallikrein binding protein can have about 85%, 90%, 91%, 92%, 93%, 94%, 95%, 96%, 97%, 98%, 99% or higher sequence identity in the HC and/or LC CDRs (e.g., HC and/or LC CDR1, 2, and/or 3) to a binding protein described herein. In some embodiments, a plasma kallikrein binding protein can have about 85%, 90%, 91%, 92%, 93%, 94%, 95%, 96%, 97%, 98%, 99% or higher sequence identity in the constant region (e.g., CH1, CH2, CH3, and/or CL1) to a binding protein described herein.

In addition, substantial identity exists when the nucleic acid segments hybridize under selective hybridization conditions (e.g., highly stringent hybridization conditions), to the complement of the strand. The nucleic acids may be present in whole cells, in a cell lysate, or in a partially purified or substantially pure form.

Motif sequences for biopolymers can include positions which can be varied amino acids. For example, the symbol "X" in such a context generally refers to any amino acid (e.g., any of the twenty natural amino acids) unless otherwise specified, e.g., to refer to any non-cysteine amino acid. Other allowed amino acids can also be indicated for example, using parentheses and slashes. For example, "(A/W/F/N/Q)" means that alanine, tryptophan, phenylalanine, asparagine, and glutamine are allowed at that particular position.

Statistical significance can be determined by any art known method. Exemplary statistical tests include: the Students T-test, Mann Whitney U non-parametric test, and Wilcoxon non-parametric statistical test. Some statistically significant relationships have a P value of less than 0.05 or 0.02. Particular binding proteins may show a difference, e.g., in specificity or binding, that are statistically significant (e.g., P value<0.05 or 0.02). The terms "induce", "inhibit", "potentiate", "elevate", "increase", "decrease" or the like, e.g., which denote distinguishable qualitative or quantitative differences between two states, and may refer to a difference, e.g., a statistically significant difference, between the two states.

A "therapeutically effective amount" refers to an amount effective, at dosages and for periods of time necessary, to achieve the desired therapeutic result. A therapeutically effective amount of the composition may vary according to factors such as the disease state, age, sex, and weight of the individual, and the ability of the protein to elicit a desired response in the individual. A therapeutically effective amount is also one in which any toxic or detrimental effect of the composition is outweighed by the therapeutically beneficial effects.

A "therapeutically effective dosage" preferably modulates a measurable parameter of a disease or disorder. For example, a therapeutically effective dosage can reduce the degree of a symptom of the disease or disorder by at least about 20%, more preferably by at least about 40%, even more preferably by at least about 60%, and still more preferably by at least about 80% as compared to the symptom prior to treatment. The ability of a compound to modulate a measurable parameter, e.g., a disease-associated parameter, can be evaluated in an animal model system predictive of efficacy in human disorders and conditions. Alternatively, this property of a composition can be evaluated by examining the ability of the compound to modulate a parameter in vitro.

"Treating" a disease or disorder in a subject (including, e.g., "treating" a subject having or at risk for developing a disease or disorder) refers to subjecting the subject to a pharmaceutical treatment, e.g., the administration of a drug, such that at least one symptom of the disease is prevented, cured, alleviated decreased, or the like.

A "disease associated with protein misfolding or aggregation" is a disease that arises, at least in part, due to a change (e.g., an obstruction) in the folding process or the stability of the folded structure of a protein. Obstruction of the folding process, increases in aggregation and de-stabilizing the native protein structure may cause loss-of-function or gain-of-function pathologies. A disease associated with protein misfolding or aggregation includes, but is not limited to: systemic amyloidosis, cryoglobulinemia, and sickle cell disease. Neurological diseases associated with protein misfolding or aggregation include Jacob-Kreutzfeld disease (associated with prion proteins), Alzheimer's disease, other amyloid diseases such as Familial amyloidotic polyneuropathy (FAP).

I. Use of Cleaved High Molecule Weight Kininogen (HMWK) as a Biomarker in Diagnosis and Prognosis Assays for Autoimmune Diseases Unexpectedly, elevated levels of cleaved HMWK were found in autoimmune diseases such as Rheumatoid Arthritis (RA), Crohn's Disease (CD) and Ulcerative Colitis (UC). Example 1 below. Thus, cleaved HMWK can serve as a reliable biomarker for diagnosing an autoimmune disease (e.g., RA, UC, and CD), monitoring the progress of such an autoimmune disease, and assessing the efficacy of a treatment for the disease.

Accordingly, described herein are diagnostic and prognostic methods for an autoimmune disease (e.g., RA, UC, and CD) based on the level of cleaved HMWK in a biosample (e.g., a plasma sample) obtained from a candidate patient.

High-molecular-weight kininogen (HMWK), also known as the Williams-Fitzgerald-Flaujeac factor or the Fitzgerald factor or the HMWK-kallikrein factor, is a protein from the blood coagulation system as well as the kinin-kallikrein system. It is a protein that adsorbs to the surface of biomaterials that come in contact with blood in vivo. High molecular-weight kininogen (HMWK) exists in the plasma as a single polypeptide (1-chain) multi-domain (domains 1-6) protein with a molecular weight of approximately 110 kDa. HMWK is cleaved by pKal within domain 4 to release the 9 amino acid, pro-inflammatory peptide bradykinin and a 2-chain form of HMWK (cleaved kininogen). The 2 chains of HMWK are the heavy chain, which contains the domains 1-3 of HMWK, and the light chain, which contains the domains 5 and 6 of HMWK. The heavy and light chains have a molecular weight of approximately 56 and 46 kilo-Daltons, respectively.

The human gene encoding HMWK is kininogen 1 (KNG1), KNG1 is transcribed and alternatively spliced to form mRNAs that encode either HMWK or low molecular weight kininogen (LMWK). An exemplary protein sequence of HMWK is provided below:

```
>gi|156231037|ref|NP_001095886.1| kininogen-1
isoform 1 precursor [Homo sapiens]
                                        (SEQ ID NO: 5)
MKLITILFLCSRLLLSLTQESQSEEIDCNDKDLFKAVDAALKKYNSQNQS

NNQFVLYRITEATKTVGSDTFYSFKYEIKEGDCPVQSGKTWQDCEYKDAA

KAAIGECIATVGKRSSTKFSVATQTCQITPAEGPVVIAQYDCLGCVHPIS

TQSPDLEPILRHGIQYFNNNTQHSSLFMLNEVKRAQRQVVAGLNFRITYS

IVQTNCSKENFLFLTPDCKSLWNGDTGECTDNAYIDIQLRIASFSQNCDI

YPGKDFVQPPTKICVGCPRDIPTNSPELEETLTHTITKLNAENNATFYFK

IDNVKKAPVQVVAGKKYFIDFVARETTCSKESNEELTESCETKKLGQSLD

CNAEVYVVPWEKKIYPTVNCQPLGMISLMKRPPGFSPFRSSRIGEIKEET

TVSPPHTSMAPAQDEERDSGKEQGHTRRHDWGHEKQRKHNLGHGHKHERD

QGHGHQRGHGLGEGHEQQHGLGHGHKFKLDDDLEHQGGHVLDHGHKHKHG

HGHGKHKNKGKKNGKHNGWKTEHLASSSEDSTTPSAQTQEKTEGPTPIPS

LAKPGVTVTFSDFQDSDLIATMMPPISPAPIQSDDDWIPDIQIDPNGLSF

NPISDFPDTTSPKCPGRPWKSVSEINPTTQMKESYYFDLTDGLS
```

Intact high molecular weight kininogen (HMWK) can be assayed, for example, using coagulant or immunological methods, e.g., radioimmunoassay (see, e.g., Kerbiriou-Nabias, D. M., Br J Haematol, 1984, 56(2):2734-86). A monoclonal antibody to the light chain of human HMWK is known. See, e.g., Reddigari, S. R. & Kaplan, A. P., Blood, 1999, 74:695-702. An assay for HMWK that relies on a chromogenic substrate can also be used. See, e.g., Scott. C. F. et al. Thromb Res, 1987, 48(6):685-700; Gallimore, M. J. et al. Thromb Res. 2004, 114(2):91-96.

Cleaved high molecular weight kininogen (HMWK), also referred to herein as "cleaved kininogen," can be assessed, for example, using methods described in Example 1, e.g., Western blot. Antibodies that specifically bind cleaved HMWK, such as, e.g., the mouse mAb clone 11H05 can be used. Additionally, cleaved HMWK may be assessed using mass spectrometry. Immunoblotting techniques for assessing levels of cleaved HMWK are known in the art. See, e.g., Buhler R. et al. Blood Coagul Fibrinolysis, 1995, 6(3):223-232.

Exemplary sequences of the heavy and light chains of cleaved kininogen are provided below.

```
>cleaved kininogen-1 heavy chain
                                        (SEQ ID NO: 6)
QESQSEEIDCNDKDLFKAVDAALKKYNSQNQSNNQFVLYRIIEATKTVGS

DTFYSFKYEIKEGDCPVQSGKTWQDCEYKDAAKAATGECTAIVGKRSSTK

FSVATQTCQITPAEGPVVTAQYDCLGCVHPISTQSPDLEPILRHGIQYFN

NNTQHSSLFMLNEVKRAQRQVVAGLNFRITYSIVQTNCSKENFLFLTPDC

KSLWNGDTGECTDNAYIDIQLRIASFSQNCDIYPGKDFVQPPTKICVGCP

RDIPTNSPELEETLTHTITKLNAENNATFYFKIDNVKKARVQVVAGKKYF

IDFVARETTCSKESNEELTESCETKKLGQSLDCNAEVYVVPWEKYIYPTV

NCQPLGMISLMK

>cleaved kininogen-1 light chain
                                        (SEQ ID NO: 7)
SSRIGEIKEETTVSPPHTSMAPAQDEERDSGKEQGHTRRHDWGHEKQRKH

NLGHGHKHERDQGHGHQRGHGLGHGHEQQHGLGHGHKFKLDDDLEHQGGH
```

-continued

VLDHGHKHKHGHGHGKHKNKGKKNGKHNGWKTEHLASSSEDSTTPSAQTQ

EKTEGPTPIPSLAKPGVTVTFSDFQDSDLIATMMPPISPAPIQSDDDWIP

DIQIDPNGLSFNPISDFPDTTSPKCPGRPWKSVSEINPTTQMKESYYFDL

TDGLS

In some examples, the levels of intact HMWK and cleaved HMWK are measured by a Western blot analysis, e.g., a Simple Western™ Protein Simple® Western blot analysis. Simple Western™ assays are known in the art (see, e.g., Rustandi et al. Qualitative and quantitative evaluation of Simon™, a new CE-based automated Western blot system as applied to vaccine development. Electrophoresis. 2012 September; 33(17):2790-7). Simple Western™ products are also available commercially (see, e.g., ProteinSimple®, Santa Clara, Calif.).

To practice any of the diagnostic and/or prognostic methods described herein, a biosample (e.g., a biofluid sample such as a plasma sample or a serum sample) can be obtained from a candidate subject (e.g., a candidate human patient) for measuring the level of cleaved HMWK. A subject can be a mammal, more preferably a human. Non-human mammals include, but are not limited to, farm animals, sport animals, pets, primates, horses, dogs, cats, mice and rats. A human subject may be a human patient suspected of having an autoimmune disease such as those described herein, e.g., RA, CD, or UC.

The biosample obtained from the subject may be a tissue or fluid sample. Examples of fluid samples include, but are not limited to, saliva, blood, plasma, serum, and urine. In some embodiments, the biosample from the subject comprises leukocytes, e.g., a blood sample. The biosample may be obtained from the patient using any method known in the art, e.g., venipuncture, biopsy, or swab. Prior to analysis, a protease inhibitor or a protease inhibitor cocktail may be added to the biosample to inhibit cleavage of HMWK in vitro. Any protease inhibitor known in the art can be used in the methods described herein.

The level of cleaved HMWK can be measured by any suitable assay known in the art (see, e.g., Molecular Cloning: A Laboratory Manual. J. Sambrook, et al., eds., Third Edition, Cold Spring Harbor Laboratory Press, Cold Spring Harbor, N.Y., 2001, Current Protocols in Molecular Biology, F. M. Ausubel, et al., eds., John Wiley & Sons, Inc., New York. Microarray technology is described in Microarray Methods and Protocols, R. Matson, CRC Press, 2009, or Current Protocols in Molecular Biology, F. M. Ausubel, et al., eds., John Wiley & Sons. Inc., New York).

In some embodiments, the level of the cleaved HMWK protein in the sample is measured. Assays for detecting cleaved HMWK protein levels include, but are not limited to, immunoassays (also referred to herein as immune-based or immuno-based assays, e.g., Western blot, immunohistochemistry and ELISA assays), Mass spectrometry, and multiplex bead-based assays. Such assays for protein level detection are known in the art.

In some examples, the level of cleaved HMWK is measured by a Western blot assay, which may involve LiCor detection as described herein. In other examples, the level of cleaved HMWK protein is measured by an immunohistochemistry assay, which may involve a binding partner, such as an antibody, that specifically binds the cleaved HMWK or specifically binds to cleaved and uncleaved HMWK.

Binding partners for protein detection can be designed using methods known in the art and as described herein. In some embodiments, the cleaved HMWK protein binding partners, e.g., anti-cleaved HMWK antibodies, bind to a part of or an entire amino acid sequence of the HMWK protein. Other examples of protein detection and quantitation methods include multiplexed immunoassays as described for example in U.S. Pat. Nos. 6,939,720 and 8,148,171, and published US Patent Application No. 2008/0255766, and protein microarrays as described for example in published US Patent Application No. 2009/0088329. Any suitable binding partner for cleaved HMWK is contemplated for detection of a cleaved HMWK level. In some embodiments, the binding partner is any molecule that binds specifically to a HMWK protein or a cleaved HMWK protein. Such a binding partner may bind to the cleaved version of HMWK (e.g., the cleaved HMWK) with much higher affinity as compared to its binding to the uncleaved HMWK. In some instances, the binding partner such as an antibody may bind only to the cleaved version of HMWK.

The antibody to be used in the method described herein can be in any form, including, but not limited to, a full-length antibody or an antigen-binding fragments thereof, such as Fab, F(ab)2. Fv, single chain antibodies, Fab and sFab fragments, F(ab')2, Fd fragments, scFv, or dAb fragments. Methods for producing antibodies are well known in the art (see, e.g., Sambrook et al, "Molecular Cloning: A Laboratory Manual" (2nd Ed.), Cold Spring Harbor Laboratory Press (1989): Lewin, "Genes IV", Oxford University Press, New York, (1990), and Roitt et al., "Immunology" (2nd Ed.), Gower Medical Publishing, London, N.Y. (1989). WO2006/040153, WO2006/122786, and WO2003/002609). See also descriptions herein.

In other embodiments, the binding partners used for measuring the level of cleaved HMWK can be non-antibody peptide molecules or aptamers that bind specifically to cleaved HMWK. Methods for producing peptide molecules and aptamers are also known in the art (see, e.g., published US Patent Application No. 2009/0075834, U.S. Pat. Nos. 7,435,542, 7,807,351, and 7,239,742).

Once the level of the cleaved HMWK in a biosample obtained from a candidate subject is determined, it can be compared with a control level for determining whether the subject has, is at risk of, or suspected of having an autoimmune disease, such as RA. CD, or UC.

In some embodiments, the control level is a level of cleaved HMWK in a control sample, such as a cell, tissue or fluid obtained from a healthy subject or population of healthy subjects, which preferably are of the same species as the candidate subject. As used herein, a healthy subject is a subject that is apparently free of the target disease (e.g., RA, CD, or UC) at the time the HMWK level is measured or has no history of the disease.

In some embodiments, a control level is a level of cleaved HMWK that is undetectable or below a background/noise level obtained using a standard method of detection (e.g., Western blot or immunohistochemistry). Preferably, the standard method of detection is the same method used for measuring the level of cleaved HMWK in the sample of the candidate subject.

The control level can also be a predetermined level. Such a predetermined level can represent the level of the cleaved HMWK in a population of subjects that do not have or are not at risk for an autoimmune disease as described herein. The predetermined level can take a variety of forms. For example, it can be single cut-off value, such as a median or mean. In some embodiments, such a predetermined level can be established based upon comparative groups, such as where one defined group is known to have a target autoimmune disease (e.g., RA, UC, or CD) and another defined group is known to not have the target autoimmune disease. Alternatively, the predetermined level can be a range, for example, a range representing the levels of the cleaved HWMK in a control population within a predetermined percentile.

The predetermined level can depend upon the particular population selected. For example, an apparently healthy (no detectable disease or prior history of a target autoimmune disease, such as RA, CD, or UC) will have a different 'normal' range of cleaved HMWK than will a population the members of which have or is at risk for the target autoimmune disease, which may be in remission. Accordingly, the predetermined levels selected may take into account the category in which a subject falls. Appropriate ranges and categories can be selected with no more than routine experimentation by those of ordinary skill in the art.

The control level as described herein can be determined by routine technology. In some examples, the control level can be obtained by performing a conventional method (e.g., the same assay for obtaining the level of cleaved HMWK in a test sample as described herein) on a control sample as also described herein. In other examples, levels of cleaved HMWK can be obtained from members of a control population and the results can be analyzed by, e.g., a computational program, to obtain the control level (a predetermined level) that represents the level of cleaved HWMK in the control population.

By comparing the level of cleaved HMWK of a sample obtained from a candidate subject to the control level as described herein, it can be determined as to whether the candidate subject has or is at risk for a target autoimmune disease. For example, if the level of the cleaved HMWK of the candidate subject deviates from the control level (e.g., elevated or decreased as compared to the control level), the candidate subject might be identified as having or at risk for the target autoimmune disease.

As used herein. "an elevated level or a level above a control" means that the level of cleaved HMWK is higher than a control level, such as a pre-determined threshold or a level of cleaved HMWK in a control sample. Control levels are described in detail herein. An elevated level of cleaved HMWK includes a cleaved HMWK level that is, for example, 1%, 5%, 10%, 20%, 30%, 40%, 50%, 60%, 70%, 80%, 90%, 100%, 150%, 200%, 300%, 400%, 500% or more above a control level. An elevated level of cleaved HMWK also includes increasing a phenomenon from a zero state (e.g., no or undetectable cleaved HMWK in a control) to a non-zero state (e.g., some cleaved HMWK or detectable cleaved HMWK in a sample).

As used herein, "a decreased level or a level below a control" means that the level of cleaved HMWK is lower than a control level, such as a pre-determined threshold or a level of cleaved HMWK in a control sample. Control levels are described in detail herein. An decreased level of cleaved HMWK includes a cleaved HMWK level that is, for example, 1%, 5%, 10%, 20%, 30%, 40%, 50%, 60%, 70%, 80%, 90%, 100%, 150%, 200%, 300%, 400%, 500% or more lower than a control level. A decreased level of cleaved HMWK also includes decreasing a phenomenon from a non-zero state (e.g., some cleaved HMWK or detectable cleaved HMWK in a sample) to a zero state (e.g., no or undetectable cleaved HMWK in a control).

In some embodiments, if an extensive level (e.g., at least 40%, 50%, 60%, 70%, 80%, 90%, or 100%) of cleaved HMWK is observed in a biosample obtained from a RA candidate patient, that candidate is diagnosed as having or at risk for RA flare. If an moderate level (e.g., about 10-30%) of cleaved HMWK is observed in a biosample obtained from a UC or CD candidate patient, that candidate is diagnosed as having or at risk for UC or CD.

Further, the level of cleaved HMWK can be used as a biomarker for monitoring the development of an autoimmune disease, such as RA, UC, and CD. For example, at least two biosamples (e.g., serum samples or plasma samples) can be obtained from a human subject having or at risk for developing a target autoimmune disease such as RA, UC, or CD at different time points. In some examples, the second biosample can be obtained at least 1 month (e.g., 3 months, 6 months, 9 months, or 12 months) after the first biosample is obtained. The levels of cleaved HMWK can be measured in the at least two biosamples. If the level of cleaved HMWK is elevated over time (e.g., the level of cleaved HMWK in a later obtained biosample is higher than that in an earlier obtained biosample by, e.g., at least 20%, 50%, 70%, 90%, 1-fold, 5-fold, 10-fold, 20-fold, 50-fold, or 100-fold), it indicated disease progress in the subject (e.g., having a higher risk for developing the autoimmune disease or the autoimmune disease exacerbates in the subject).

Moreover, the level of cleaved HMWK can also be used as a biomarker to assess the responsiveness of a subject to an anti-autoimmune treatment, e.g., those described herein. For example, multiple biosamples can be obtained from a human patient subjected to a treatment during the course of the treatment and the levels of cleaved HMWK can be measured following routine technology such as those described herein. If the level of cleaved HMWK in a human patient subject to a treatment remains decreases over the course of the treatment (e.g., the level of cleaved HMWK in a later obtained biosample is lower than that in an earlier obtained biosample, e.g., by at least 20%, 50%, 70%, 80%, 90%, 100%, 2-fold, 5-fold, 10-fold, 50-fold, or 100-fold), it indicates that the human patient is responsive to the treatment. On the other hand, if the level of cleaved HMWK remains substantially the same over the course of the treatment (e.g., the level of cleaved HMWK in a later obtained biosample is substantially identical to or decreases by less than 20%, e.g., 15%, 10%, or 5% relative to that of an earlier obtained biosample), it indicates that the human patient is not responsive to the treatment.

When a subject is identified as having or at risk for an autoimmune disease (e.g., RA, UC, or CD) by any of the methods described herein, a suitable treatment can be performed to treat the disease. In some examples, the subject can be treated by one or more pKal inhibitors as described herein. When a subject is determined as not responsive to a treatment by any of the methods described herein, a higher dose and/or frequency of dosage of a therapeutic (e.g., a pKal inhibitor) can be administered to the subject. Alternatively, the subject can switch to a different treatment. On the other hand, the dosage or frequency of dosage of the therapeutic agent is maintained, lowered, or ceased in a subject identified as responsive to the treatment or not in need of further treatment.

II. Treatment of Autoimmune Diseases

Also described herein are methods for treating diseases associated with the plasma kallikrein (pKal) system, including, but not limited to, diabetic macular edema, retinal proliferation, brain trauma, acute spinal cord injury, localized amyloidosis, autoimmune diseases such as psoriasis, multiple aclerosis, inflammatory bowel disease, rheumatoid arthritis, vasculitis, systemic lupus erythematosis nephritis, systemic mastocytosis, severe burns, and neuropathic pain (diabetic and post-herpetic neuralgia). Such methods comprise administering to a subject in need of the treatment (e.g., a human patient having or at risk for the disease) an effective amount of one or more kallikrein inhibitors via a suitable route.

(A) Plasma Kallikrein

Exemplary plasma kallikrein sequences against which plasma kallikrein binding proteins may be developed can include human, mouse, or rat plasma kallikrein amino acid sequences, a sequence that is 80%, 85%, 90%, 95%, 96%, 97%, 98%, or 99% identical to one of these sequences, or a fragment thereof, e.g., of a sequence provided below.

The sequence of human plasma kallikrein that was used in selections and subsequent screening of binding proteins is shown below (accession number NP_000883.2). The human plasma kallikrein (86 kDa) that was used was purified from human plasma and activated with factor XIIa by a commercial vendor. Factor XIIa activates prekallikrein by cleaving the polypeptide sequence at a single site (between Arg371-Ile372, cleavage site marked by "/" in the sequence below) to generate active plasma kallikrein, which then consists of two disulfide linked polypeptides; a heavy chain of approximately 52 kDa and a catalytic domain of approximately 34 kDa [Colman and Schmaier, (1997) "Contact System: A Vascular Biology Modulator With Anticoagulant, Profibrinolytic, Antiadhesive, and Proinflammatory Attributes" Blood, 90, 3819-3843]

The human, mouse, and rat prekallikrein amino acid sequences, and the mRNA sequences encoding the same, are illustrated below. The sequences of prekallikrein are the same as plasma kallikrein, except that active plasma kallikrein (pkal) has the single polypeptide chain cleaved at a single position (indicated by the "/") to generate two chains. The sequences provided below are full sequences that include signal sequences. On secretion from the expressing cell, it is expected that the signal sequences are removed.

Exemplary plasma kallikrein proteins from various species can be found in GeneBank under accession numbers NP_000883.2 (human pKal protein), NM_000892 (human pKal mRNA), NP_032481.1 (mouse pKal protein), NM_008455.2 (mouse pKal mRNA). NP_036857.2 (rat pKal protein), and NM_012725 (rat pKal mRNA).

(B) Kallikrein Inhibitors

Kunitz Domain Inhibitors.

A number of useful inhibitors of kallikrein, either tissue and/or plasma kallikrein, include a Kunitz domain. Exemplary Kunitz domain inhibitors are described in US Patent Application Publication US20100183625, which is incorporated by reference herein.

As used herein, a "Kunitz domain" is a polypeptide domain having at least 51 amino acids and containing at least two, and preferably three, disulfides. The domain is folded such that the first and sixth cysteines, the second and fourth, and the third and fifth cysteines form disulfide bonds (e.g., in a Kunitz domain having 58 amino acids, cysteines can be present at positions corresponding to amino acids 5, 14, 30, 38, 51, and 55, according to the number of the BPTI homologous sequences provided below, and disulfides can form between the cysteines at position 5 and 55, 14 and 38, and 30 and 51), or, if two disulfides are present, they can form between a corresponding subset of cysteines thereof. The spacing between respective cysteines can be within 7, 5, 4, 3, 2, 1 or 0 amino acids of the following spacing between positions corresponding to: 5 to 55, 14 to 38, and 30 to 51, according to the numbering of the BPTI sequence provided below. The BPTI sequence can be used as a reference to refer to specific positions in any generic Kunitz domain. Comparison of a Kunitz domain of interest to BPTI can be performed by identifying the best fit alignment in which the number of aligned cysteines in maximized.

The 3D structure (at high resolution) of the Kunitz domain of BPTI is known. One of the X-ray structures is deposited in the Brookhaven Protein Data Bank as "6PTI". The 3D structure of some BPTI homologues (Eigenbrot et al., (1990) Protein Engineering, 3(7):591-598; Hynes et al., (1990) Biochemistry, 29:10018-10022) are known. At least eighty one Kunitz domain sequences are known. Known human homologues include three Kunitz domains of LACI also known as tissue factor pathway inhibitor (TFPI) (Wun et al., (1988) J. Biol. Chem. 263(13):6001-6004; Girard et al., (1989) Nature, 338:518-20; Novotny el al. (1989) J. Biol. Chem., 264(31):18832-18837) two Kunitz domains of Inter-α-Trypsin Inhibitor. APP-I (Kido et al., (1988) J. Biol. Chem., 263(34):18104-18107), a Kunitz domain from collagen, three Kunitz domains of TFPI-2 (Sprecher et al., (1994) PNAS USA, 91:3353-3357), the Kunitz domains of hepatocyte growth factor activator inhibitor type 1, the Kunitz domains of Hepatocyte growth factor activator inhibitor type 2, the Kunitz domains described in U.S. Patent Publication No.: 2004-0152633. LACI is a human serum phosphoglycoprotein with a molecular weight of 39 kDa containing three Kunitz domains.

The Kunitz domains above are referred to as LACI-K1 (residues 50 to 107), LACI-K2 (residues 121 to 178), and LACI-K3 (213 to 270). The cDNA sequence of LACI is reported in Wun et al. (J. Biol. Chem., 1988, 263(13):6001-6004). Girard et al. (Nature, 1989, 338:518-20) reports mutational studies in which the P1 residues of each of the three Kunitz domains were altered. LACI-K1 inhibits Factor Vila (F.VIIa) when F.VIIa is complexed to tissue factor and LACI-K2 inhibits Factor Xa.

Proteins containing exemplary Kunitz domains include the following, with SWISS-PROT Accession Numbers in parentheses:

A4_HUMAN (P05067), A4_MACFA (P53601), A4_MACMU (P29216),
A4_MOUSE (P12023), A4_RAT (P08592), A4_SAISC (Q95241),
AMBP_PLEPL (P36992), APP2_HUMAN (Q06481), APP2_RAT (P15943),
AXP1_ANTAF (P81547), AXP2_ANTAF (P81548), BPT1_BOVIN (P00974),
BPT2_BOVIN (P04815), CA17_HUMAN (Q02388), CA36_CHICK (P15989),
CA36_HUMAN (P12111), CRPI_BOOMI (P81162), ELAC_MACEU (O62845),
ELAC_TRIVU (Q29143), EPPI_HUMAN (O95925), EPPI_MOUSE (Q9DA01),
HTIB_MANSE (P26227), IBP_CARCR (P00993), IBPC_BOVIN (P00976),
IBPI_TACTR (P16044), IBPS_BOVIN (P00975), ICS3_BOMMO (P07481),
IMAP_DROFU (P11424), IP52_ANESU (P10280), ISC1_BOMMO (P10831),
ISC2_BOMMO (P10832), ISH1_STOHE (P31713), ISH2_STOHE (P81129),
ISIK_HELPO (P00994), ISP2_GALME (P81906), IVB1_BUNFA (P25660),
IVB1_BUNMU (P00987), IVB1_VIPAA (P00991), IVB2_BUNMU (P00989),
IVB2_DABRU (P00990), IVB2_HEMHA (P00985), IVB2_NAJNI (P00986),

IVB3_VIPAA (P00992), IVBB_DENPO (P00983), IVBC_NAJNA (P19859),
IVBC_OPHHA (P82966), IVBE_DENPO (P00984), IVBI_DENAN (P00980),
IVBI_DENPO (P00979), IVBK_DENAN (P00982), IVBK_DENPO (P00981),
IVBT_ERIMA (P24541), IVBT_NAJNA (P20229), MCPI_MELCP (P82968),
SBPI_SARBU (P26228), SPT3_HUMAN (P49223), TKD1_BOVIN (Q28201),
TKD1_SHEEP (Q29428), TXCA_DENAN (P81658), UPTI_PIG (Q29100),
AMBP_BOVIN (P00978), AMBP_HUMAN (P02760), AMBP_MERUN (Q62577),
AMBP_MESAU (Q60559), AMBP_MOUSE (Q07456), AMBP_PIG (P04366),
AMBP_RAT (Q64240), IATR_HORSE (P04365), IATR_SHEEP (P13371),
SPT1_HUMAN (O43278), SPT1_MOUSE (Q9R097), SPT2_HUMAN (O43291),
SPT2_MOUSE (Q9WU03), TFP2_HUMAN (P48307), TFP2_MOUSE (O35536),
TFPI_HUMAN (P10646), TFPI_MACMU (Q28864), TFPI_MOUSE (O54819),
TFPI_RABIT (P19761), TFPI_RAT (Q02445), YN81_CAEEL (Q03610)

A variety of methods can be used to identify a Kunitz domain from a sequence database. For example, a known amino acid sequence of a Kunitz domain, a consensus sequence, or a motif (e.g., the ProSite Motif) can be searched against the GenBank sequence databases (National Center for Biotechnology Information, National Institutes of Health, Bethesda Md.), e.g., using BLAST; against Pfam database of HMMs (Hidden Markov Models) (e.g., using default parameters for Pfam searching; against the SMART database; or against the ProDom database. For example, the Pfam Accession Number PF00014 of Pfam Release 9 provides numerous Kunitz domains and an HMM for identify Kunitz domains. A description of the Pfam database can be found in Sonhammer et al. (1997) Proteins 28(3):405-420 and a detailed description of HMMs can be found, for example, in Gribskov et al. (1990) Meth. Enzymol. 183:146-159; Gribskov et al. (1987) Proc. Natl. Acad. Sci. USA 84:4355-4358; Krogh et al. (1994) J. Mol. Biol. 235:1501-1531; and Stultz el al. (1993) Protein Sci. 2:305-314. The SMART database (Simple Modular Architecture Research Tool. EMBL, Heidelberg, Del.) of HMMs as described in Schultz et at (1998), Proc. Natl. Acad. Sci. USA 95:5857 and Schultz et al. (2000) Nucl. Acids Res 28:231. The SMART database contains domains identified by profiling with the hidden Markov models of the HMMer2 search program (R. Durbin et al. (1998) Biological sequence analysis: probabilistic models of proteins and nucleic acids. Cambridge University Press). The database also is annotated and monitored. The ProDom protein domain database consists of an automatic compilation of homologous domains (Corpet et al. (1999). Nucl. Acids Res. 27:263-267). Current versions of ProDom are built using recursive PSI-BLAST searches (Altschul et al. (1997) Nucleic Acids Res. 25:3389-3402; Gouzy et al. (1999) Computers and Chemistry 23:333-340) of the SWISS-PROT 38 and TREMBL protein databases. The database automatically generates a consensus sequence for each domain. Prosite lists the Kunitz domain as a motif and identifies proteins that include a Kunitz domain. See, e.g., Falquet et al. Nucleic Acids Res. 30:235-238(2002).

Kunitz domains interact with target protease using, primarily, amino acids in two loop regions ("binding loops"). The first loop region is between about residues corresponding to amino acids 13-20 of BPTI. The second loop region is between about residues corresponding to amino acids 31-39 of BPTI. An exemplary library of Kunitz domains varies one or more amino acid positions in the first and/or second loop regions. Particularly useful positions to vary, when screening for Kunitz domains that interact with kallikrein or when selecting for improved affinity variants, include: positions 13, 15, 16, 17, 18, 19, 31, 32, 34, and 39 with respect to the sequence of BPTI. At least some of these positions are expected to be in close contact with the target protease. It is also useful to vary other positions, e.g., positions that are adjacent to the aforementioned positions in the three-dimensional structure.

The "framework region" of a Kunitz domain is defined as those residues that are a part of the Kunitz domain, but specifically excluding residues in the first and second binding loops regions, i.e., about residues corresponding to amino acids 13-20 of BPTI and 31-39 of BPTI. Conversely, residues that are not in the binding loop may tolerate a wider range of amino acid substitution (e.g., conservative and/or non-conservative substitutions).

In one embodiment, these Kunitz domains are variant forms of the looped structure including Kunitz domain 1 of human lipoprotein-associated coagulation inhibitor (LACI) protein. LACI contains three internal, well-defined, peptide loop structures that are paradigm Kunitz domains (Girard, T. et al., 1989. Nature, 338:518-520). Variants of Kunitz domain 1 of LACI described herein have been screened, isolated and bind kallikrein with enhanced affinity and specificity (see, for example, U.S. Pat. Nos. 5,795,865 and 6,057,287). These methods can also be applied to other Kunitz domain frameworks to obtain other Kunitz domains that interact with kallikrein, e.g., plasma kallikrein. Useful modulators of kallikrein function typically bind and/or inhibit kallikrein, as determined using kallikrein binding and inhibition assays.

An exemplary polypeptide that includes a Kunitz domain that inhibits plasma kallikrein has or includes the amino acid sequence defined by amino acids 3-60 of SEQ ID NO:2. Another exemplary polypeptide that includes a Kunitz domain that inhibits plasma kallikrein has or includes the amino acid sequence of SEQ ID NO:2.

An exemplary polypeptide includes the amino acid sequence:

(SEQ ID NO: 1)
Xaa1 Xaa2 Xaa3 Xaa4 Cys Xaa6 Xaa7 Xaa8 Xaa9 Xaa10

Xaa11 Gly Xaa13 Cys Xaa15 Xaa16 Xaa17 Xaa18 Xaa19

Xaa20 Xaa21 Xaa22 Xaa23 Xaa24 Xaa25 Xaa26 Xaa27

Xaa28 Xaa29 Cys Xaa31 Xaa32 Phe Xaa34 Xaa35 Gly

Gly Cys Xaa39 Xaa40 Xaa41 Xaa42 Xaa43 Xaa44 Xaa45

Xaa46 Xaa47 Xaa48 Xaa49 Xaa50 Cys Xaa52 Xaa53

Xaa54 Cys Xaa56 Xaa57 Xaa58.

"Xaa" refers to a position in a peptide chain that can be any of a number of different amino acids. In a first example, Xaa can by any amino acid except cysteine. In another example, one or more of the following apply: Xaa10 can be Asp or Glu; Xaa11 can be Asp, Gly, Ser, Val, Asn, Ile, Ala or Thr; Xaa13 can be Pro, Arg, His, Asn, Ser, Thr, Ala, Gly, Lys or Gln; Xaa15 can be Arg, Lys, Ala, Ser, Gly, Met, Asn or Gln; Xaa16 can be Ala, Gly, Ser, Asp or Asn; Xaa17 can be Ala, Asn, Ser, Ile, Gly, Val, Gln or Thr, Xaa18 can be His, Leu, Gln or Ala; Xaa19 can be Pro, Gln, Leu, Asn or Ile; Xaa21 can be Trp, Phe, Tyr, His or Ile; Xaa31 can be Glu, Asp, Gln, Asn, Ser, Ala, Val, Leu, Ile or Thr; Xaa32 can be Glu, Gln, Asp Asn, Pro, Thr, Leu, Ser, Ala, Gly or Val; Xaa34 can be Ile, Thr, Ser, Val, Ala, Asn, Gly or Leu; Xaa35 can be Tyr, Trp or Phe; Xaa39 can be Glu, Gly, Ala, Ser or Asp. Amino acids Xaa6, Xaa7, Xaa8, Xaa9, Xaa20, Xaa24, Xaa25, Xaa26, Xaa27, Xaa28, Xaa29, Xaa41, Xaa42, Xaa44, Xaa46, Xaa47, Xaa48, Xaa49, Xaa50, Xaa52, Xaa53 and Xaa54 can be any amino acid.

Additionally, each of the first four (Xaa1, Xaa2, Xaa3. Xaa4) and at last three 9 Xaa56, Xaa57 or Xaa58) amino acids of SEQ ID NO: 1 can optionally be present or absent and can be any amino acid, if present, e.g., any non-cysteine amino acid In one embodiment, the polypeptide has a sequence with one or more of the following properties: Xaa11 can be Asp, Gly, Ser or Val; Xaa13 can be Pro, Arg, His or Asn; Xaa15 can be Arg or Lys; Xaa16 can be Ala or Gly; Xaa17 can be Ala, Asn, Ser or Ile; Xaa18 can be His, Leu or Gln; Xaa19 can be Pro. Gln or Leu; Xaa21 can be Trp or Phe; Xaa31 is Glu; Xaa32 can be Glu or Gln; Xaa34 can be Ile, Thr or Ser, Xaa35 is Tyr, and Xaa39 can be Glu, Gly or Ala.

An exemplary polypeptide can include the following amino acids: Xaa10 is Asp; Xaa11 is Asp; Xaa13 can be Pro or Arg; Xaa15 is Arg; Xaa16 can be Ala or Gly; Xaa17 is Ala; Xaa18 is His; Xaa19 is Pro; Xaa21 is Trp; Xaa31 is Glu; Xaa32 is Glu; Xaa34 can be Ile or Ser, Xaa35 is Tyr; and Xaa39 is Gly.

It is also possible to use portions of the polypeptides described herein. For example, polypeptides could include binding domains for specific kallikrein epitopes. For example, the binding loops of Kunitz domains can by cyclized and used in isolation or can be grafted onto another domain, e.g., a framework of another Kunitz domain. It is also possible to remove one, two, three, or four amino acids from the N-terminus of an amino acid sequence described herein, and/or one, two, three, four, or five amino acids from the C-terminus of an amino acid sequence described herein.

Additional examples of sequence include those that differ by at least one amino acid, but fewer than seven, six, five, four, three, or two amino acids differences relative to an amino acid sequence described herein, e.g., an amino acid sequence provided above. In one embodiment, fewer than three, two, or one differences are in one of the binding loops. For example, the first binding loop may have no differences relative to an amino acid sequence described herein, e.g., an amino acid sequence provided above. In another example, neither the first nor the second binding loop differs from an amino acid sequence described herein, e.g., an amino acid sequence provided above.

Still others polypeptides that inhibit plasma kallikrein include an about 58-amino acid sequence of amino acids 3-60 of SEQ ID NO:2 or the PEP-1 polypeptide having the 60-amino acid sequence of SEQ ID NO:2. The terms "PEP-1" and "DX-88" as used herein both refer to the 60-amino acid sequence of SEQ ID NO:2. In one embodiment, the polypeptide is other than aprotinin, e.g., differs from aprotinin, by at least one, two, three, five, ten, or fifteen amino acids.

Polypeptides described herein can be made synthetically using any standard polypeptide synthesis protocol and equipment. For example, the stepwise synthesis of a polypeptide can be carried out by the removal of an amino (N) terminal-protecting group from an initial (i.e., carboxyterminal) amino acid, and coupling thereto of the carboxyl end of the next amino acid in the sequence of the polypeptide. This amino acid is also suitably protected. The carboxyl group of the incoming amino acid can be activated to react with the N-terminus of the bound amino acid by formation into a reactive group such as formation into a carbodiimide, a symmetric acid anhydride, or an "active ester" group such as hydroxybenzotriazole or pentafluorophenyl esters. Preferred solid-phase peptide synthesis methods include the BOC method, which utilizes tert-butyloxycarbonyl as the l-amino protecting group, and the FMOC method, which utilizes 9-fluorenylmethloxycarbonyl to protect the alpha-amino of the amino acid residues. Both methods are well known to those of skill in the art (Stewart, J, and Young, J., Solid-Phase Peptide Synthesis (W. H. Freeman Co., San Francisco 1989); Merrifield, J., 1963. Am. Chem. Soc., 85:2149-2154; Bodanszky, M. and Bodanszky, A., The Practice of Peptide Synthesis (Springer-Verlag, New York 1984)). If desired, additional amino- and/or carboxy-terminal amino acids can be designed into the amino acid sequence and added during polypeptide synthesis.

Polypeptides can also be produced using recombinant technology. Recombinant methods can employ any of a number of cells and corresponding expression vectors, including but not limited to bacterial expression vectors, yeast expression vectors, baculovirus expression vectors, mammalian viral expression vectors, and the like. A polypeptide described herein can be produced by a transgenic animal, e.g., in the mammary gland of a transgenic animal. In some cases, it could be necessary or advantageous to fuse the coding sequence for a polypeptide that inhibits kallikrein (e.g., a polypeptide that includes a Kunitz domain) to another coding sequence in an expression vector to form a fusion polypeptide that is readily expressed in a host cell. Part or all of the additional sequence can be removed, e.g., by protease digestion.

An exemplary recombinant expression system for producing a polypeptide that inhibits kallikrein (e.g., a polypeptide that includes a Kunitz domain) is a yeast expression vector, which permits a nucleic acid sequence encoding the amino acid sequence for the inhibitor polypeptide to be linked in the same reading frame with a nucleotide sequence encoding the MATα prepro leader peptide sequence of *Saccharomyces cerevisiae*, which in turn is under the control of an operable yeast promoter. The resulting recombinant yeast expression plasmid can be transformed by standard methods into the cells of an appropriate, compatible yeast host, which cells are able to express the recombinant protein from the recombinant yeast expression vector. Preferably, a host yeast cell transformed with such a recombinant expression vector is also able to process the fusion protein to provide an active inhibitor polypeptide. An other exemplary yeast host for producing recombinant polypeptides is *Pichia pastoris*.

As noted above, polypeptides that inhibit kallikrein can include a Kunitz domain polypeptide described herein. Some polypeptides can include an additional flanking sequence, preferably of one to six amino acids in length, at the amino and/or carboxy-terminal end, provided such additional amino acids do not significantly diminish kallikrein binding affinity or kallikrein inhibition activity so as to preclude use in the methods and compositions described herein. Such additional amino acids can be deliberately added to express a polypeptide in a particular recombinant host cell or can be added to provide an additional function, e.g., to provide a linker to another molecule or to provide an affinity moiety that facilitates purification of the polypeptide. Preferably, the additional amino acid(s) do not include cysteine, which could interfere with the disulfide bonds of the Kunitz domain.

An exemplary Kunitz domain polypeptide includes the amino acid sequence of residues 3-60 of SEQ ID NO:2. When expressed and processed in a yeast fusion protein expression system (e.g., based on the integrating expression plasmid pHIL-D2), such a Kunitz domain polypeptide retains an additional amino terminal Glu-Ala dipeptide from the fusion with the MATalpha-prepro leader peptide sequence of S. cerevisiae. When secreted from the yeast host cell, most of the leader peptide is processed from the fusion protein to yield a functional polypeptide (referred to herein as "PEP-1") having the amino acid sequence of SEQ ID NO:2.

A typical Kunitz domain, e.g., that includes, SEQ ID NO: 1, contains a number of invariant positions, e.g., positions corresponding to position 5, 14, 30, 33, 38, 45, 51 and 55 in the BPTI numbering scheme are cysteine. The spacing between these positions may vary to the extent allowable within the Kunitz domain fold, e.g., such that three disulfide bonds are formed. Other positions such as, for example, positions 6, 7, 8, 9, 20, 24, 25, 26, 27, 28, 29, 41, 42, 44, 46, 47, 48, 49, 50, 52, 53 and 54, or positions corresponding to those positions, can be any amino acid (including non-genetically encoded occurring amino acids). In a particularly preferred embodiment, one or more amino acids correspond to that of a native sequence. In another embodiment, at least one variable position is different from that of the native sequence. In yet another preferred embodiment, the amino acids can each be individually or collectively substituted by a conservative or non-conservative amino acid substitution.

Conservative amino acid substitutions replace an amino acid with another amino acid of similar chemical nature and may have no affect on protein function. Non-conservative amino acid substitutions replace an amino acid with another amino acid of dissimilar chemical structure. Examples of conserved amino acid substitutions include, for example, Asn→Gln, Arg→Lys and Ser→Thr. In a preferred embodiment, 1, 2, 3, 4, 5, 6, 7, 8, 9, 10, 11, 12, 13, 14, 15, 16, 17, 18, 19, 20 and/or 21 of these amino acids can be independently or collectively, in any combination, selected to correspond to the corresponding position of SEQ ID NO:2.

Other positions, for example, positions 10, 11, 13, 15, 16, 17, 18, 19, 21, 22, 23, 31, 32, 34, 35, 39, 40, 43 and 45, or positions corresponding to those positions can be any of a selected set of amino acids. For example, SEQ ID NO: 1 defines a set of possible sequences. Each member of this set contains, for example, a cysteine at positions 5, 14, 30, 51 and 55, and any one of a specific set of amino acids at positions 10, 11, 13, 15, 16, 17, 18, 19, 21, 22, 23, 31, 32, 34, 35, 39, 40, 43 and 45, or positions corresponding to those positions. In a preferred embodiment, 1, 2, 3, 4, 5, 6, 7, 8, 9, 10, 11, 12, 13, 14, 15, 16, 17, 18 and/or 19 of these amino acids can be independently or collectively, in any combination, selected to correspond to the corresponding position of SEQ ID NO:2. The polypeptide preferably has at least 80%, 85%, 90%, 95, 97, 98, or 99% identity to SEQ ID NO:2.

The comparison of sequences and determination of percent homology between two sequences can be accomplished using a mathematical algorithm. In a preferred embodiment, the percent homology between two amino acid sequences is determined using the Needleman and Wunsch (1970), J. Mol. Biol. 48:444-453, algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent homology between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a homology limitation) are a Blossum 62 scoring matrix with a gap penalty of 12, a gap extend penalty of 4, and a frameshift gap penalty of 5.

Binding Protein Inhibitors.

In other embodiments, the inhibitors of kallikrein are binding proteins, such as antibodies. Exemplary binding proteins such as antibodies are described, e.g., in PCT Publication WO2012/094587 and US Patent Application Publication US 20100183625, both of which are incorporated herein by reference in their entirety.

In one aspect, the disclosure features a protein (e.g., an isolated protein) that binds to plasma kallikrein (e.g., human plasma kallikrein) and includes at least one immunoglobulin variable region. For example, the protein includes a heavy chain (HC) immunoglobulin variable domain sequence and/or a light chain (LC) immunoglobulin variable domain sequence. The protein can bind to and inhibit plasma kallikrein, e.g., human plasma kallikrein.

The protein can include one or more of the following characteristics: (a) a human CDR or human framework region; (b) the HC immunoglobulin variable domain sequence comprises one or more (e.g., 1, 2, or 3) CDRs that are at least 85, 88, 89, 90, 91, 92, 93, 94, 95, 96, 97, 98, 99, or 100% identical to a CDR of a HC variable domain described herein; (c) the LC immunoglobulin variable domain sequence comprises one or more (e.g., 1, 2, or 3) CDRs that are at least 85, 88, 89, 90, 91, 92, 93, 94, 95, 96, 97, 98, 99, or 100% identical to a CDR of a LC variable domain described herein; (d) the LC immunoglobulin variable domain sequence is at least 85, 88, 89, 90, 91, 92, 93, 94, 95, 96, 97, 98, 99, or 100% identical to a LC variable domain described herein (e.g., overall or in framework regions or CDRs); (e) the HC immunoglobulin variable domain sequence is at least 85, 88, 89, 90, 91, 92, 93, 94, 95, 96, 97, 98, 99, or 100% identical to a HC variable domain described herein (e.g., overall or in framework regions or CDRs); (f) the protein binds an epitope bound by a protein described herein, or competes for binding with a protein described herein; (g) a primate CDR or primate framework region; (h) the HC immunoglobulin variable domain sequence comprises a CDR1 that differs by at least one amino acid but by no more than 2 or 3 amino acids from the CDR1 of a HC variable domain described herein; (i) the HC immunoglobulin variable domain sequence comprises a CDR2 that differs by at least one amino acid but by no more than 2, 3, 4, 5, 6, 7, or 8 amino acids from the CDR2 of a HC variable domain described herein; (j) the HC immunoglobulin variable domain sequence comprises a CDR3 that differs by at least one amino acid but by no more than 2, 3, 4, 5, or 6 amino acids from the CDR3 of a HC variable domain described herein; (k) the LC immunoglobulin variable domain sequence comprises a CDR1 that differs by at least one amino acid but by no more than 2, 3, 4, or 5 amino acids from the CDR1 of a LC variable domain described herein; (l) the LC immunoglobulin variable domain sequence comprises a CDR2 that differs by at least one amino acid but by no more than 2, 3, or 4 amino acids from the CDR2 of a LC variable domain described herein; (m) the LC immunoglobulin variable domain sequence comprises a CDR3 that differs by at least one amino acid but by no more than 2, 3, 4, or 5 amino acids from the CDR3 of a LC variable domain described herein; (n) the LC immunoglobulin variable domain sequence differs by at least one amino acid but by no more than 2, 3, 4, 5, 6, 7, 8, 9, or 10 amino acids from a LC variable domain described herein (e.g., overall or in framework regions or CDRs); and (o) the HC immunoglobulin variable domain sequence differs by at least one amino acid but by no more than 2, 3, 4, 5, 6, 7, 8, 9, or 10 amino acids from a HC variable domain described herein (e.g., overall or in framework regions or CDRs).

The plasma kallikrein binding protein may be an isolated protein (e.g., at least 70, 80, 90, 95, or 99% free of other proteins). The plasma kallikrein binding protein may inhibit plasma kallikrein, e.g., human plasma kallikrein. In some embodiments, the plasma kallikrein binding protein does not bind prekallikrein (e.g., human prekallikrein), but binds to the active form of plasma kallikrein (e.g., human plasma kallikrein).

In certain embodiments, the protein binds at or near the active site of the catalytic domain of plasma kallikrein, or a fragment thereof, or binds an epitope that overlaps with the active site of plasma kallikrein. In some aspects, the protein binds the same epitope or competes for binding with a protein described herein.

In some embodiments, the protein competes with or binds the same epitope as M162-A04, M160-G12, M142-H08, X63-G06, X101-A01 (also referred to herein as DX-2922), X81-B01, X67-D03, X67-G04, X81-B01, X67-D03, X67-G04, X115-B07, X115-D05, X115-E09, X115-H06, X115-A03, X115-D01, X115-F02, X124-G01 (also referred to herein as DX-2930), X115-G04, M29-D09, M145-D11, M06-D09 and M35-G04. See, e.g., PCT Publication WO2012/094587 and US Patent Application Publication US 20100183625 In some embodiments, the protein binds to one or more amino acids that form the catalytic triad of plasma kallikrein: His434. Asp483, and/or Ser578 (numbering based on the human sequence).

In some embodiments, the protein binds to one or more amino acids of Ser479. Tyr563, and/or Asp585 (numbering based on the human sequence).

The protein can bind to plasma kallikrein, e.g., human plasma kallikrein, with a binding affinity of at least $10^5$, $10^6$, $10^7$, $10^8$, $10^9$, $10^{10}$ and $10^{11}$ M$^{-1}$. In one embodiment, the protein binds to human plasma kallikrein with a $K_{off}$ slower than $1\times10^{-3}$, $5\times10^{-4}$ s$^{-1}$, or $1\times10^{-4}$ s$^{-1}$. In one embodiment, the protein binds to human plasma kallikrein with a $K_{on}$ faster than $1\times10^2$, $1\times10^3$, or $5\times10^3$ M$^{-1}$s$^{-1}$. In one embodiment, the protein binds to plasma kallikrein, but does not binds to tissue kallikrein and/or plasma prekallikrein (e.g., the protein binds to tissue kallikrein and/or plasma prekallikrein less effectively (e.g., 5-, 10-, 50-, 100-, or 1000-fold less or not at all, e.g., as compared to a negative control) than it binds to plasma kallikrein.

In one embodiment, the protein inhibits human plasma kallikrein activity, e.g., with a Ki of less than $10^{-5}$, $10^{-6}$, $10^{-7}$, $10^{-8}$, $10^{-9}$, and $10^{-10}$ M. The protein can have, for example, an IC50 of less than 100 nM, 10 nM or 1 nM. For example, the protein may modulate plasma kallikrein activity, as well as the production of Factor XIIa (e.g., from Factor XII) and/or bradykinin (e.g., from high-molecular-weight kininogen (HMWK)). The protein may inhibit plasma kallikrein activity, and/or the production of Factor XIIa (e.g., from Factor XII) and/or bradykinin (e.g., from high-molecular-weight kininogen (HMWK)). The affinity of the protein for human plasma kallikrein can be characterized by a $K_D$ of less than 100 nm, less than 10 nM, or less than 1 nM. In one embodiment, the protein inhibits plasma kallikrein, but does not inhibit tissue kallikrein (e.g., the protein inhibits tissue kallikrein less effectively (e.g., 5-, 10-, 50-, 100-, or 1000-fold less or not at all, e.g., as compared to a negative control) than it inhibits plasma kallikrein.

In some embodiments, the protein has an apparent inhibition constant ($K_{i,app}$) of less than 1000, 500, 100, or 10 nM.

Plasma kallikrein binding proteins may be antibodies. Plasma kallikrein binding antibodies may have their HC and LC variable domain sequences included in a single polypeptide (e.g., scFv), or on different polypeptides (e.g., IgG or Fab).

In a preferred embodiment, the protein is an antibody (e.g., a human antibody) having the light and/or heavy chains of antibodies selected from the group consisting of M162-A04, M160-G12, M142-H08, X63-G06, X101-A01 (also referred to herein as DX-2922), X81-B01, X67-D03, X67-G04, X81-B01, X67-D03, X67-G04, X115-B07, X115-D05, X115-E09, X115-H06, X115-A03, X115-D01, X115-F02, X124-G01 (also referred to herein as DX-2930), X115-G104, M29-D09, M145-D11, M06-D09 and M35-G04.

In a preferred embodiment, the protein is an antibody (e.g., a human antibody) having one or more (e.g., 1, 2, or 3) heavy chain CDRs selected from the corresponding CDRs of the group of heavy chains consisting of M162-A04, MI 60-G12, M142-H08, X63-G06, X101-A01 (also referred to herein as DX-2922), X81-B01, X67-D03, X67-G04, X81-B01, X67-D03, X67-G04, X115-B07, X115-D05, X115-E09, X115-H06, X115-A03, X115-D01, X115-F02, X124-G01 (also referred to herein as DX-2930), X115-G04, M29-D09, M145-D11, M06-D09 and M35-G04.

In a preferred embodiment, the protein is an antibody (e.g., a human antibody) having one or more (e.g., 1, 2, or 3) light chain CDRs selected from the corresponding CDRs of the group of light chains consisting of M162-A04, M160-G12, M142-H08, X63-G06, X101-A01 (also referred to herein as DX-2922), X81-B01, X67-D03, X67-G04, X81-B01, X67-D03, X67-G04, X115-B07, X115-D05, X115-E09, X115-H06, X115-A03, X115-D01, X115-F02, X124-G01 (also referred to herein as DX-2930), X115-G04, M29-D09, M145-D11, M06-D09 and M35-G04.

In a preferred embodiment, the protein is an antibody (e.g., a human antibody) having one or more (e.g., 1, 2, or 3) heavy chain CDRs and one or more (e.g., 1, 2, or 3) light chain CDRs selected from the corresponding CDRs of the group of light chains consisting of M162-A04, M160-G12, M142-H08, X63-G06, X101-A01 (also referred to herein as DX-2922), X81-B01, X67-D03, X67-G04, X81-B01, X67-D03, X67-G04, X115-B07, X115-D05, X115-E09, X115-H06, X115-A03, X115-D01, X115-F02, X124-G01 (also referred to herein as DX-2930), X115-G04, M29-D09, M145-D11, M06-D09 and M35-G04.

In one embodiment, the HC and LC variable domain sequences are components of the same polypeptide chain. In another, the HC and LC variable domain sequences are components of different polypeptide chains. For example, the protein is an IgG, e.g., IgG1, IgG2, IgG3, or IgG4. The protein can be a soluble Fab. In other implementations the protein includes a Fab2', scFv, minibody, scFv::Fc fusion, Fab::HSA fusion. HSA::Fab fusion. Fab::HSA::Fab fusion, or other molecule that comprises the antigen combining site of one of the binding proteins herein. The VH and VL regions of these Fabs can be provided as IgG, Fab. Fab2, Fab2', scFv, PEGylated Fab. PEGylated scFv, PEGylated Fab2. VH::CH1::HSA+LC, HSA::VH::CH1+LC, LC:: HSA+VH::CH1, HSA::LC+VH::CH1, or other appropriate construction.

In one embodiment, the protein is a human or humanized antibody or is non-immunogenic in a human. For example, the protein includes one or more human antibody framework regions, e.g., all human framework regions, or framework regions at least 85, 88, 89, 90, 91, 92, 93, 94, 95, 96, 97, 98, 99% identical to human framework regions. In one embodiment, the protein includes a human Fc domain, or an Fe domain that is at least 95, 96, 97, 98, or 99% identical to a human Fc domain.

In one embodiment, the protein is a primate or primatized antibody or is non-immunogenic in a human. For example, the protein includes one or more primate antibody framework regions, e.g., all primate framework regions, or framework regions at least 85, 88, 89, 90, 91, 92, 93, 94, 95, 96, 97, 98, 99% identical to primate framework regions. In one embodiment, the protein includes a primate Fc domain, or an Fc domain that is at least 95, 96, 97, 98, or 99% identical to a primate Fc domain. "Primate" includes humans (*Homo sapiens*), chimpanzees (*Pan troglodytes* and *Pan paniscus* (bonobos)), gorillas (*Gorilla gorilla*), gibons, monkeys, lemurs, aye-ayes (*Daubentonia madagascariensis*), and tarsiers.

In some embodiments, the affinity of the primate antibody for human plasma kallikrein is characterized by a $K_D$ of less than 1000, 500, 100 or 10 nM, e.g., less than 10 nM or less than 1 nM.

In one embodiment, the protein includes human framework regions, or framework regions that are at least 95, 96, 97, 98, or 99% identical to human framework regions. In certain embodiments, the protein includes no sequences from mice or rabbits (e.g., is not a murine or rabbit antibody).

In some aspects, the disclosure provides the use of proteins (e.g., binding proteins, e.g., antibodies) (e.g., the proteins described herein) that bind to plasma kallikrein (e.g., human plasma kallikrein) and include at least one immunoglobin variable region in methods for treating a disease or disorder described herein. For example, the plasma kallikrein binding protein includes a heavy chain (HC) immunoglobulin variable domain sequence and a light chain (LC) immunoglobulin variable domain sequence. A number of exemplary plasma kallikrein binding proteins are described herein.

Antibodies may be discovered by screening a library using a kallikrein target, as well as by other methods. For example, kallikrein protein or a region thereof can be used as an antigen in a non-human animal, e.g., a rodent. Humanized antibodies can be generated by replacing sequences of the Fv variable region that are not directly involved in antigen binding with equivalent sequences from human Fv variable regions. General methods for generating humanized antibodies are provided by Morrison, S. L., 1985, *Science* 229:1202-1207, by Oi et al., 1986, *BioTechniques* 4:214, and by Queen et al. U.S. Pat. Nos. 5,585,089, 5,693,761 and 5,693,762. Those methods include isolating, manipulating, and expressing the nucleic acid sequences that encode all or part of immunoglobulin Fv variable regions from at least one of a heavy or light chain. Numerous sources of such nucleic acid are available. For example, nucleic acids may be obtained from a hybridoma producing an antibody against a predetermined target, as described above. The recombinant DNA encoding the humanized antibody, or fragment thereof, can then be cloned into an appropriate expression vector.

Immunoglobin kallikrein binding proteins (e.g., IgG or Fab kallikrein binding proteins) may be modified to reduce immunogenicity. Reduced immunogenicity is desirable in kallikrein binding proteins intended for use as therapeutics, as it reduces the chance that the subject will develop an immune response against the therapeutic molecule. Techniques useful for reducing immunogenicity of kallikrein binding proteins include deletion/modification of potential human T cell epitopes and 'germlining' of sequences outside of the CDRs (e.g., framework and Fc).

A kallikrein-binding antibody may be modified by specific deletion of human T cell epitopes or "deimmunization" by the methods disclosed in WO 98/52976 and WO 00/34317. Briefly, the heavy and light chain variable regions of an antibody are analyzed for peptides that bind to MHC Class II; these peptides represent potential T-cell epitopes (as defined in WO 98/52976 and WO 00/34317). For detection of potential T-cell epitopes, a computer modeling approach termed "peptide threading" can be applied, and in addition a database of human MHC class 11 binding peptides can be searched for motifs present in the VH and VL sequences, as described in WO 98/52976 and WO 00/34317. These motifs bind to any of the 18 major MHC class II DR allotypes, and thus constitute potential T cell epitopes. Potential T-cell epitopes detected can be eliminated by substituting small numbers of amino acid residues in the variable regions, or preferably, by single amino acid substitutions. As far as possible conservative substitutions are made, often but not exclusively, an amino acid common at this position in human germline antibody sequences may be used. Human germline sequences are disclosed in Tomlinson, I. A. et al., 1992, *J. Mol. Biol.* 227:776-798; Cook, G. P. et al., 1995, *Immunol. Today* Vol. 16 (5): 237-242; Chothia, D. et al., 1992, *J. Mol. Bio.* 227:799-817. The V BASE directory provides a comprehensive directory of human immunoglobulin variable region sequences (compiled by Tomlinson, I. A. et al. MRC Centre for Protein Engineering, Cambridge, UK). After the deimmunizing changes are identified, nucleic acids encoding $V_H$ and $V_L$ can be constructed by mutagenesis or other synthetic methods (e.g., de novo synthesis, cassette replacement, and so forth). Mutagenized variable sequence can, optionally, be fused to a human constant region, e.g., human IgG1 or K constant regions.

In some cases a potential T cell epitope will include residues which are known or predicted to be important for antibody function. For example, potential T cell epitopes are usually biased towards the CDRs. In addition, potential T cell epitopes can occur in framework residues important for antibody structure and binding. Changes to eliminate these potential epitopes will in some cases require more scrutiny, e.g., by making and testing chains with and without the change. Where possible, potential T cell epitopes that overlap the CDRs were eliminated by substitutions outside the CDRs. In some cases, an alteration within a CDR is the only option, and thus variants with and without this substitution should be tested. In other cases, the substitution required to remove a potential T cell epitope is at a residue position within the framework that might be critical for antibody binding. In these cases, variants with and without this substitution should be tested. Thus, in some cases several variant deimmunized heavy and light chain variable regions were designed and various heavy/light chain combinations tested in order to identify the optimal deimmunized antibody. The choice of the final deimmunized antibody can then be made by considering the binding affinity of the different variants in conjunction with the extent of deimmunization, i.e., the number of potential T cell epitopes remaining in the variable region. Deimmunization can be, used to modify any antibody, e.g., an antibody that includes a non-human sequence, e.g., a synthetic antibody, a murine antibody other non-human monoclonal antibody, or an antibody isolated from a display library.

Kallikrein binding antibodies are "germlined" by reverting one or more non-germline amino acids in framework regions to corresponding germline amino acids of the antibody, so long as binding properties are substantially retained. Similar methods can also be used in the constant region, e.g., in constant immunoglobulin domains.

Antibodies that bind to kallikrein, e.g., an antibody described herein, may be modified in order to make the variable regions of the antibody more similar to one or more germline sequences. For example, an antibody can include one, two, three, or more amino acid substitutions, e.g., in a framework, CDR, or constant region, to make it more similar to a reference germline sequence. One exemplary germlining method can include identifying one or more germline sequences that are similar (e.g., most similar in a particular database) to the sequence of the isolated antibody. Mutations (at the amino acid level) are then made in the isolated antibody, either incrementally or in combination with other mutations. For example, a nucleic acid library that includes sequences encoding some or all possible germline mutations is made. The mutated antibodies are then evaluated, e.g., to identify an antibody that has one or more additional germline residues relative to the isolated antibody and that is still useful (e.g., has a functional activity). In one embodiment, as many germline residues are introduced into an isolated antibody as possible.

In one embodiment, mutagenesis is used to substitute or insert one or more germline residues into a framework and/or constant region. For example, a germline framework and/or constant region residue can be from a germline sequence that is similar (e.g., most similar) to the non-variable region being modified. After mutagenesis, activity (e.g., binding or other functional activity) of the antibody can be evaluated to determine if the germline residue or residues are tolerated (i.e., do not abrogate activity). Similar mutagenesis can be performed in the framework regions.

Selecting a germline sequence can be performed in different ways. For example, a germline sequence can be selected if it meets a predetermined criteria for selectivity or similarity, e.g., at least a certain percentage identity, e.g., at least 75, 80, 85, 90, 91, 92, 93, 94, 95, 96, 97, 98, 99, or 99.5% identity. The selection can be performed using at least 2, 3, 5, or 10 germline sequences. In the case of CDR1 and CDR2, identifying a similar germline sequence can include selecting one such sequence. In the case of CDR3, identifying a similar germline sequence can include selecting one such sequence, but may including using two germline sequences that separately contribute to the amino-terminal portion and the carboxy-terminal portion. In other implementations more than one or two germline sequences are used, e.g., to form a consensus sequence.

In one embodiment, with respect to a particular reference variable domain sequence, e.g., a sequence described herein, a related variable domain sequence has at least 30, 40, 50, 60, 70, 80, 90, 95 or 100% of the CDR amino acid positions that are not identical to residues in the reference CDR sequences, residues that are identical to residues at corresponding positions in a human germline sequence (i.e., an amino acid sequence encoded by a human germline nucleic acid).

In one embodiment, with respect to a particular reference variable domain sequence, e.g., a sequence described herein, a related variable domain sequence has at least 30, 50, 60, 70, 80, 90 or 100% of the FR regions identical to FR sequence from a human germline sequence, e.g., a germline sequence related to the reference variable domain sequence.

Accordingly, it is possible to isolate an antibody which has similar activity to a given antibody of interest, but is more similar to one or more germline sequences, particularly one or more human germline sequences. For example, an antibody can be at least 90, 91, 92, 93, 94, 95, 96, 97, 98, 99, or 99.5% identical to a germline sequence in a region outside the CDRs (e.g., framework regions). Further, an antibody can include at least 1, 2, 3, 4, or 5 germline residues in a CDR region, the germline residue being from a germline sequence of similar (e.g., most similar) to the variable region being modified. Germline sequences of primary interest are human germline sequences. The activity of the antibody (e.g., the binding activity as measured by $K_A$) can be within a factor or 100, 10, 5, 2, 0.5, 0.1, and 0.001 of the original antibody.

Germline sequences of human immunoglobin genes have been determined and are available from a number of sources, including the international ImMunoGeneTics information System® (IMGT), available via the world wide web at imgt.cines.fr, and the V BASE directory (compiled by Tomlinson, I. A. et al. MRC Centre for Protein Engineering, Cambridge, UK, available via the world wide web at vbase.mrc-cpe.cam.ac.uk).

Exemplary germline reference sequences for $V_{kappa}$ include: O12/O2, O18/O8, A20, A30, L14, L1, L15, L4/18a, L5/L19, L8, L23, L9, L24, L11, L12, O11/O1, A17, A1, A18, A2, A19/A3, A23, A27, A11, L2/L116, L6, L20, L25, B3, B2, A26/A10, and A14. See, e.g., Tomlinson et al., 1995. *EMBO J.* 14(18):4628-3.

A germline reference sequence for the HC variable domain can be based on a sequence that has particular canonical structures, e.g., 1-3 structures in the H1 and H2 hypervariable loops. The canonical structures of hypervariable loops of an immunoglobulin variable domain can be inferred from its sequence, as described in Chothia et al., 1992, *J. Mol. Biol.* 227:799-817; Tomlinson et al., 1992, *J. Mol. Biol.* 227:776-798); and Tomlinson et al., 1995, *EMBO J.* 14(18):4628-38. Exemplary sequences with a 1-3 structure include: DP-1, DP-8, DP-12, DP-2, DP-25, DP-15, DP-7, DP-4, DP-31, DP-32, DP-33, DP-35, DP-40, 7-2, hv3005, hv3005f3, DP-46, DP-47, DP-58, DP-49, DP-50, DP-51, DP-53, and DP-54.

Useful polypeptides can also be encoded by a nucleic acid that hybridizes to a nucleic acid that encodes a polypeptide described herein. The nucleic acids can hybridize under medium, high, or very high stringency conditions. As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1-6.3.6, which is incorporated by reference. Aqueous and nonaqueous methods are described in that reference and either can be used. Specific hybridization conditions referred to herein are as follows: (1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); (2) medium stringency hybridization conditions in 6×SSC at about 45° C., followed by one or more washes in 0.2×SSC, 0.1% SDS at 60° C.; (3) high stringency hybridization conditions in 6×SSC at about 45° C., followed by one or more washes in 0.2×SSC, 0.1% SDS at 65° C.; and (4) very high stringency hybridization conditions are 0.5M sodium phosphate, 7% SDS at 65° C., followed by one or more washes at 0.2×SSC, 1% SDS at 65° C.

Protein Production.

Standard recombinant nucleic acid methods can be used to express a protein that binds to plasma kallikrein. Generally, a nucleic acid sequence encoding the protein is cloned into a nucleic acid expression vector. Of course, if the protein includes multiple polypeptide chains, each chain can be cloned into an expression vector, e.g., the same or different vectors, that are expressed in the same or different cells.

Antibody Production.

Some antibodies, e.g., Fabs, can be produced in bacterial cells, e.g., *E. coli* cells. For example, if the Fab is encoded by sequences in a phage display vector that includes a suppressible stop codon between the display entity and a bacteriophage protein (or fragment thereof), the vector nucleic acid can be transferred into a bacterial cell that cannot suppress a stop codon. In this case, the Fab is not fused to the gene III protein and is secreted into the periplasm and/or media.

Antibodies can also be produced in eukaryotic cells. In one embodiment, the antibodies (e.g., scFv's) are expressed in a yeast cell such as *Pichia* (see, e.g., Powers et al., 2001, J. Immunol. Methods. 251:123-35), *Hanseula*, or *Saccharomyces*.

In one preferred embodiment, antibodies are produced in mammalian cells. Preferred mammalian host cells for expressing the clone antibodies or antigen-binding fragments thereof include Chinese Hamster Ovary (CHO cells) (including dhfr-CHO cells, described in Urlaub and Chasin, 1980, Proc. Natl. Acad. Sci. USA 77:4216-4220, used with a DHFR selectable marker, e.g., as described in Kaufman and Sharp, 1982, Mol. Biol. 159:601 621), lymphocytic cell lines, e.g., NS0 myeloma cells and SP2 cells, COS cells, HEK293T cells (J. Immunol. Methods (2004) 289(1-2):65-80), and a cell from a transgenic animal, e.g., a transgenic mammal. For example, the cell is a mammary epithelial cell.

In addition to the nucleic acid sequence encoding the diversified immunoglobulin domain, the recombinant expression vectors may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr host cells with methotrexate selection/amplification) and the neo gene (for G418 selection).

In an exemplary system for recombinant expression of an antibody, or antigen-binding portion thereof, a recombinant expression vector encoding both the antibody heavy chain and the antibody light chain is introduced into dhfr CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. For example, some antibodies can be isolated by affinity chromatography with a Protein A or Protein G coupled matrix.

For antibodies that include an Fc domain, the antibody production system may produce antibodies in which the Fc region is glycosylated. For example, the Fc domain of IgG molecules is glycosylated at asparagine 297 in the CH2 domain. This asparagine is the site for modification with biantennary-type oligosaccharides. It has been demonstrated that this glycosylation is required for effector functions mediated by Fcg receptors and complement C1q (Burton and Woof, 1992, Adv. Immunol. 51:1-84; Jefferis et al., 1998, Immunol. Rev. 163:59-76). In one embodiment, the Fc domain is produced in a mammalian expression system that appropriately glycosylates the residue corresponding to asparagine 297. The Fc domain can also include other eukaryotic post-translational modifications.

Antibodies can also be produced by a transgenic animal. For example, U.S. Pat. No. 5,849,992 describes a method of expressing an antibody in the mammary gland of a transgenic mammal. A transgene is constructed that includes a milk-specific promoter and nucleic acids encoding the antibody of interest and a signal sequence for secretion. The milk produced by females of such transgenic mammals includes, secreted-therein, the antibody of interest. The antibody can be purified from the milk, or for some applications, used directly.

(C) Modifications

It is possible to modify polypeptides that inhibit kallikrein in a variety of ways. For example, the polypeptides can be attached to one or more polyethylene glycol moieties to stabilize the compound or prolong retention times, e.g., by at least 2, 4, 5, 8, 10, 15, 20, 50, 100, 500 or 1000 fold.

In one embodiment, a kallikrein binding protein is physically associated with a moiety that improves its stabilization and/or retention in circulation, e.g., in blood, serum, lymph, or other tissues, e.g., by at least 1.5, 2, 5, 10, or 50 fold. For example, a kallikrein binding protein can be associated with a polymer, e.g., a substantially non-antigenic polymer, such as a polyalkylene oxide or polyethylene oxide. Suitable polymers will vary substantially by weight. Polymers having molecular number average weights ranging from about 200 to about 35,000 (or about 1,000 to about 15.000, and 2,000 to about 12.500) can be used. For example, a kallikrein binding protein can be conjugated to a water soluble polymer, e.g., hydrophilic polyvinyl polymers, e.g. polyvinylalcohol and polyvinylpyrrolidone. A plurality of polymer moieties can be attached to one polypeptide, e.g., at least two, three, or four such moieties, e.g., having an average molecular weight of about 2.000 to 7.000 Daltons. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained.

For example, the polypeptide can be conjugated to a water soluble polymer, e.g., a hydrophilic polyvinyl polymer, e.g. polyvinylalcohol and polyvinylpyrrolidone. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained. Additional useful polymers include polyoxyalkylenes such as polyoxyethylene, polyoxypropylene, and block copolymers of polyoxyethylene and polyoxypropylene (Pluronics); polymethacrylates; carbomers; branched or unbranched polysaccharides which comprise the saccharide monomers D-mannose, D- and L-galactose, fucose, fructose, D-xylose, L-arabinose, D-glucuronic acid, sialic acid, D-galacturonic acid, D-mannuronic acid (e.g. polymannuronic acid, or alginic acid). D-glucosamine, D-galactosamine, D-glucose and neuraminic acid including homopolysaccharides and heteropolysaccharides such as lactose, amylopectin, starch, hydroxyethyl starch, amylose, dextrane sulfate, dextran, dextrins, glycogen, or the polysaccharide subunit of acid mucopolysaccharides, e.g. hyaluronic acid; polymers of sugar alcohols such as polysorbitol and polymannitol; heparin or heparan.

It is possible for one or more framework and/or CDR amino acid residues of a binding protein to include one or more mutations (e.g., substitutions (e.g., conservative substitutions or substitutions of non-essential amino acids), insertions, or deletions) relative to a binding protein described herein. A plasma kallikrein binding protein may have mutations (e.g., substitutions (e.g., conservative substitutions or substitutions of non-essential amino acids), insertions, or deletions) (e.g., at least one, two, three, or four, and/or less than 15, 12, 10, 9, 8, 7, 6, 5, 4, 3, or 2 mutations) relative to a binding protein described herein, e.g., mutations which do not have a substantial effect on protein function. The mutations can be present in framework regions, CDRs, and/or constant regions. In some embodiments, the mutations are present in a framework region. In some embodiments, the mutations are present in a CDR. In some embodiments, the mutations are present in a constant region. Whether or not a particular substitution will be tolerated, i.e., will not adversely affect biological properties, such as binding activity can be predicted, e.g., by evaluating whether the mutation is conservative or by the method of Bowie, et al. (1990) Science 247:1306-1310.

A kallikrein inding protein can also be associated with a carrier protein, e.g., a serum albumin, such as a human serum albumin. For example, a translational fusion can be used to associate the carrier protein with the kallikrein binding protein.

(D) Treating Auto-Immune Diseases Associated with Kallikrein System

One or more of the pKal inhibitors as described herein can be used to treating diseases associated with the pKal system, including, but not limited to diabetic macular edema, retinal proliferation, brain trauma, acute spinal cord injury, localized amyloidosis, autoimmune diseases such as psoriasis, multiple aclerosis, inflammatory bowel disease, rheumatoid arthritis, vasculitis, systemic lupus erythematosis nephritis, systemic mastocytosis, severe burns, and neuropathic pain (diabetic and post-herpetic neuralgia).

A subject who is at risk (e.g., a human patient) for developing an autoimmune or the other pKal-associated diseases mentioned herein can be, e.g., a subject who has a disease associated with the development of the disease, a subject who has been exposed to an environmental factor associated with the development of the disease, a subject who has a family history of the disease, or a subject who carries a gene associated with the development of the disease.

The subjects can be humans in need of treatment for an autoimmune or one of the other pKal-associated disease (e.g., humans having the disease or at risk of developing the disease) or nonhuman subjects (e.g., an animal model of an autoimmune or one of the other pKal-associated disease).

In some embodiments, the subject is a subject (e.g., a human patient) who is at risk for developing an autoimmune disease such as rheumatoid arthritis (RA), Crohn's disease (CD) or Ulcerative colitis (UC). Autoimmune diseases are diseases caused by an abnormal immune response to a subject's own body. The abnormal immune response may be against a certain organ or tissue, depending on the type of autoimmune disease.

RA is a chronic inflammatory disease generally affecting the joints, such as the synovial joints of the hands and/or feet. The inflammatory response in RA often causes destruction of cartilage and fusion of the joints, resulting in loss of function and mobility. Symptoms of RA include swollen and/or warm joints, stiffness, rheumatoid nodules, fatigue, fever, and weight loss. Exemplary treatments for RA include physical therapy, orthoses, analgesics, anti-inflammatory drugs, steroids, and disease-modifying antirheumatic drugs (DMARDs).

CD is an inflammatory bowel disease that can affect any part of the GI tract. Symptoms include abdominal pain, diarrhea, fever, fatigue and weight loss. Exemplary treatments for CD include corticosteroids, 5-aminosalicylic acid drugs, azathioprine, methotrexate, infliximab, adalimumab, certolizumab, natalizumab, dietary adjustments, and surgery.

UC is an inflammatory bowel disease that generally affects the large intestine. Symptoms include bloody and/or mucus-containing diarrhea, weight loss, anemia, abdominal pain, and blood in the rectum. Exemplary treatments for UC include 5-aminosalicylic acid drugs, corticosteroids, azathioprine, budesonide, infliximab, adalimumab, and surgery.

(E) Combination Therapy

The plasma kallikrein inhibitor may be administered along with another therapeutic as part of a combination therapy for a disease or disorder described herein.

Combination therapy with a kallikrein inhibitor and another therapeutic agent may be provided in multiple different configurations. In situations where the kallikrein inhibitor is to be administered by intraarticular injection, the kallikrein inhibitor and the therapeutic agent may be co-administered as a single composition, or they may be administered by separate injections. In some situations, the kallikrein inhibitor and the therapeutic agent are administered in close temporal proximity (e.g., a short time interval between the injections, such as during the same treatment session), or more widely spaced, depending on the desired schedule of administration for the two components of the combination therapy. When the kallikrein inhibitor is to be administered by systemic (parenteral) administration, the kallikrein inhibitor and the therapeutic agent may be administered in close temporal proximity or more widely spaced, depending on the intended dosing schedule for the two components of the combination therapy.

In other embodiments, the kallikrein inhibitor may be administered in combination with other compounds useful for treating or preventing inflammation, which is involved in autoimmune diseases. Exemplary anti-inflammatory agents include, for example, steroids (e.g., Cortisol, cortisone, fludrocortisone, prednisone, 6[alpha]-methylprednisone, triamcinolone, betamethasone or dexamethasone), nonsteroidal anti-inflammatory drugs (NSAIDS (e.g., aspirin, acetaminophen, tolmetin, ibuprofen, mefenamic acid, piroxicam, nabumetone, rofecoxib, celecoxib, etodolac or nimesulide). In another embodiment, the other therapeutic agent is an antibiotic (e.g., vancomycin, penicillin, amoxicillin, ampicillin, cefotaxime, ceftriaxone, cefixime, rifampinmetronidazole, doxycycline or streptomycin). In another embodiment, the other therapeutic agent is a PDE4 inhibitor (e.g., roflumilast or rolipram). In another embodiment, the other therapeutic agent is an antihistamine (e.g., cyclizine, hydroxyzine, promethazine or diphenhydramine).

Further examples of anti-inflammatory agents include, for example, aceclofenac, acemetacin, e-acetamidocaproic acid, acetaminophen, acetaminosalol, acetanilide, acetylsalicylic acid, S-adenosylmethionine, alclofenac, alclometasone, alfentanil, algestone, allylprodine, alminoprofen, aloxiprin, alphaprodine, aluminum bis(acetylsalicylate), amcinonide, amfenac, aminochlorthenoxazin, 3-amino-4-hydroxybutyric acid, 2-amino-4-picoline, aminopropylon, aminopyrine, amixetrine, ammonium salicylate, ampiroxicam, amtolmetin guacil, anileridine, antipyrine, antrafenine, apazone, beclomethasone, bendazac, benorylate, benoxaprofen, benzpiperylon, benzydamine, benzylmorphine, bermoprofen, betamethasone, betamethasone-17-valerate, bezitramide, [alpha]-bisabolol, bromfenac, p-bromoacetanilide, 5-bromosalicylic acid acetate, bromosaligenin, bucetin, bucloxic acid, bucolome, budesonide, bufexamac, bumadizon, buprenorphine, butacetin, butibufen, butorphanol, carbamazepine, carbiphene, caiprofen, carsalam, chlorobutanol, chloroprednisone, chlorthenoxazin, choline salicylate, cinchophen, cinmetacin, ciramadol, clidanac, clobetasol, clocortolone, clometacin, clonitazene, clonixin, clopirac, cloprednol, clove, codeine, codeine methyl bromide, codeine phosphate, codeine sulfate, cortisone, cortivazol, cropropamide, crotethamide and cyclazocine.

Further examples of anti-inflammatory agents include deflazacort, dehydrotestosterone, desomorphine, desonide, desoximetasone, dexamethasone, dexamethasone-21-isonicotinate, dexoxadrol, dextromoramide, dextropropoxyphene, deoxycorticosterone, dezocine, diampromide, diamorphone, diclofenac, difenamizole, difenpiramide, ditlorasone, ditlucortolone, diflunisal, ditluprednate, dihydrocodeine, dihydrocodeinone enol acetate, dihydromorphine, dihydroxyaluminum acetylsalicylate, dimenoxadol, dimepheptanol, dimethylthiambutene, dioxaphetyl butyrate, dipipanone, diprocetyl, dipyrone, ditazol, droxicam, emorfazone, enfenamic acid, enoxolone, epirizole, eptazocine, etersalate, ethenzamide, ethoheptazine, ethoxazene, ethylmethylthiambutene, ethylmorphine, etodolac, etofenamate, etonitazene, eugenol, felbinac, fenbufen, fenclozic acid, fendosal, fenoprofen, fentanyl, fentiazac, fepradinol, feprazone, floctafenine, fluazacort, flucloronide, flufenamic acid, flumethasone, flunisolide, flunixin, flunoxaprofen, fluocinolone acetonide, fluocinonide, fluocinolone acetonide, fluocortin butyl, fluocoitolone, fluoresone, fluorometholone, fluperolone, flupirtine, fluprednidene, fluprednisolone, fluproquazone, flurandrenolide, flurbiprofen, fluticasone, formocortal and fosfosal.

Further examples of anti-inflammatory agents include gentisic acid, glafenine, glucametacin, glycol salicylate, guaiazulene, halcinonide, halobetasol, halometasone, haloprednone, heroin, hydrocodone, hydro cortamate, hydrocortisone, hydrocortisone acetate, hydrocortisone succinate, hydrocortisone hemisuccinate, hydrocortisone 21-lysinate, hydrocortisone cypionate, hydromorphone, hydroxypethidine, ibufenac, ibuprofen, ibuproxam, imidazole salicylate, indomethacin, indoprofen, isofezolac, isoflupredone, isoflupredone acetate, isoladol, isomethadone, isonixin, isoxepac, isoxicam, ketobemidone, ketoprofen, ketorolac, p-lactophenetide, lefetamine, levallorphan, levorphanol, levophenacylmorphan, lofentanil, lonazolac, lornoxicam, loxoprofen, lysine acetylsalicylate, mazipredone, meclofenamic acid, medrysone, mefenamic acid, meloxicam, meperidine, meprednisone, meptazinol, mesalamine, metazocine, methadone, methotrimeprazine, methylprednisolone, methylprednisolone acetate, methylprednisolone sodium succinate, methylprednisolone suleptnate, metiazinic acid, metofoline, metopon, mofebutazone, mofezolac, mometasone, morazone, morphine, morphine hydrochloride, morphine sulfate, morpholine salicylate and myrophine.

Further examples of anti-inflammatory agents include nabumetone, nalbuphine, nalorphine, 1-naphthyl salicylate, naproxen, narceine, nefopam, nicomorphine, nifenazone, niflumic acid, nimesulide, 5'-nitro-2'-propoxyacetanilide, norlevorphanol, normethadone, normorphine, norpipanone, olsalazine, opium, oxaceprol, oxametacine, oxaprozin, oxycodone, oxymorphone, oxyphenbutazone, papaveretum, paramethasone, paranyline, parsalmide, pentazocine, perisoxal, phenacetin, phenadoxone, phenazocine, phenazopyridine hydrochloride, phenocoll, phenoperidine, phenopyrazone, phenomorphan, phenyl acetylsalicylate, phenylbutazone, phenyl salicylate, phenyramidol, piketoprofen, piminodine, pipebuzone, piperylone, pirazolac, piritramide, piroxicam, pirprofen, pranoprofen, prednicarbate, prednisolone, prednisone, prednival, prednylidene, proglumetacin, proheptazine, promedol, propacetamol, properidine, propiram, propoxyphene, propyphenazone, proquazone, protizinic acid, proxazole, ramifenazone, remifentanil, rimazolium metilsulfate, salacetamide, salicin, salicylamide, salicylamide o-acetic acid, salicylic acid, salicylsulfuric acid, salsalate, salverine, simetride, sufentanil, sulfasalazine, sulindac, superoxide dismutase, suprofen, suxibuzone, talniflumate, tenidap, tenoxicam, terofenamate, tetrandrine, thiazolinobutazone, tiaprofenic acid, tiaramide, tilidine, tinoridine, tixocortol, tolfenamic acid, tolmetin, tramadol, triamcinolone, triamcinolone acetonide, tropesin, viminol, xenbucin, ximoprofen, zaltoprofen and zomepirac.

(F) Administration

The patient is generally a human, but may also be a non-human mammal. Human patients include adults, e.g., patients between ages 19-25, 26-40, 41-55, 56-75, and 76 and older, and pediatric patients, e.g., patients between ages 0-2, 3-6, 7-12, and 13-18.

The term "pharmaceutically acceptable" composition refers to a non-toxic carrier or excipient that may be administered to a patient, together with a kallikrein inhibitor described herein. The carrier or excipient is chosen to be compatible with the biological or pharmacological activity of the composition. The kallikrein inhibitors (and, in the case of combination therapy, other therapeutic agent) described herein can be administered locally or systemically by any suitable means for delivery of an inhibitory amount of the inhibitor and/or other therapeutic agent to a patient including but not limited to systemic administrations such as, for example, intravenous and inhalation. Parenteral administration is particularly preferred for the kallikrein inhibitor.

For parenteral administration, the kallikrein inhibitor can be injected intravenously, intramuscularly, intraperitoneally, or subcutaneously. Subcutaneous injection and i.v. administration are preferred routes for parenteral administration. Also useful is local (intraarticular) injection.

Typically, compositions for administration by injection are solutions in sterile isotonic aqueous buffer (e.g., sodium/potassium phosphate buffered saline). Other pharmaceutically acceptable carriers include, but are not limited to, sterile water, saline solution, and buffered saline (including buffers like phosphate or acetate), alcohol, vegetable oils, polyethylene glycols, gelatin, lactose, amylose, magnesium stearate, talc, silicic acid, paraffin, etc. Where necessary, the composition can also include a solubilizing agent and a local anesthetic such as lidocaine to ease pain at the site of the injection, preservatives, stabilizers, wetting agents, emulsifiers, salts, lubricants, etc. as long as they do not react deleteriously with the active compounds. Similarly, the composition can comprise conventional excipients, e.g., pharmaceutically acceptable organic or inorganic carrier substances suitable for parenteral, enteral or intranasal application which do not deleteriously react with the active compounds. Generally, the ingredients will be supplied either separately or mixed together in unit dosage form, for example, as a dry lyophilized powder or water free concentrate in a hermetically sealed container such as an ampoule, sachette, or vial indicating the quantity of active agent in activity units. Where the composition is to be administered by infusion, it can be dispensed with an infusion bottle containing sterile pharmaceutical grade "water for injection" or saline. Where the composition is to be administered by injection, a container (e.g., ampoule or vial) of sterile water for injection or saline can be provided so that the ingredients can be mixed prior to administration.

Exemplary formulations for subcutaneous administration of an isolated kallikrein inhibitor include buffered solutions containing a buffering agent (e.g., histidine or phosphate buffer) and a cryoprotectant (e.g., sucrose or sucrose and mannitol, optionally including a dextran such as dextran 40), and may be lyophilized for storage and distribution as described in U.S. Pub. App. No. 2007-0213275 (U.S. Ser. No. 11/716,278, filed Mar. 9, 2007).

In one embodiment, the kallikrein inhibitor is administered to a patient as an intravenous infusion according to any approved procedure. In another embodiment, the kallikrein inhibitor is administered to a patient as a subcutaneous bolus. In another embodiment, the kallikrein inhibitor is administered to a patient by intraarticular injection. I.V. and intraarticular administration are typically carried out by a health care professional in a clinical setting (e.g., hospital, urgent care, or doctor's office), but subcutaneous injections may be self-administered or administered by a health care professional.

Parameters that can be evaluated for determining a dose of the kallikrein inhibitor for systemic administration, are described below with regards to DX-88 (a non-naturally occurring kallikrein inhibitor, SEQ ID NO:2). The total amount of circulating prekallikrein in plasma is reported to be approximately 500 nM to 600 nM (Silverberg et al., "The Contact System and Its Disorders," in Blood: Principles and Practice of Hematology. Handin, R. et al., eds, J B Lippincott Co., Philadelphia. 1995). If all prekallikrein is activated, about 520 nmoles/L of DX-88 (DX88) can be used to inhibit kallikrein in a stoichiometric manner. An individual having 5 L of plasma would require a dose of 2.6 micromoles DX-88, or approximately 18 mg based on the molecular weight of DX-88 of 7,054 Daltons. This was calculated as follows: the $K_i$ of DX88 is 0.025 nM. When it is desired to have a concentration of plasma kallikrein (PK) of, e.g., 1 nM, the following formula for a tight binding inhibitor indicates that the concentration of free DX-88 is 12.0 nM. Thus, the total amount of DX-88 needed would be 499+12 or 511 nM.

$$[DX88_{total}] = \frac{K_{i,app}[pKal-DX88]}{[DX88_{free}]} + [pKal-DX88]$$

$$511 \text{ nM} = (0.025)(499)/(1) + (499)$$

The dose can be reduced proportionally if not all of the prekallikrein is activated or if a portion of the kallikrein is deactivated by an endogenous inhibitor, e.g., C1 esterase inhibitor (C1INH). Thus, in certain embodiments, about 5, 10, 15, 20, 30, 40, 60.80, 120, 250, 500, 600, 700, 800, 1000 mg of DX-88 can be administered to a subject, in a single dose or in one or more doses spread over a twenty-four hour period. Consideration of several other factors may provide a more accurate estimation of the dose of DX-88 required in practice, such as patient age, weight, and severity of the condition 0.

In some embodiments, the kallikrein inhibitor polypeptide is administered in a dose of about 1-500 mg/m$^2$, preferably about 1-250 mg/m$^2$, 1-100 mg/m$^2$.

(G) Devices and Kits

Pharmaceutical compositions that include the kallikrein inhibitor can be administered with a medical device. The device can designed with features such as portability, room temperature storage, and ease of use so that it can be used in settings outside of a hospital or emergency room/urgent care facility (e.g., by the patient or a caregiver in the home or in a doctor's office). The device can include, e.g., one or more housings for storing pharmaceutical preparations that include an isolated kallikrein inhibitor, and can be configured to deliver one or more unit doses of the agent or agents.

I.V. administration may be by bolus or infusion, using appropriate injection or infusion devices (e.g., catheters, infusion pumps, implants, and the like). Subcutaneous injection may be as an infusion, for example using a catheter and infusion pump or implantable device. Many other devices, implants, delivery systems, and modules are also known.

When the kallikrein inhibitor is distributed as a lyophilized powder, it must be reconstituted prior to use. Manual reconstitution (e.g., manual addition of diluent to the lyophilized formulation by injection through an injection port into the container containing the lyophilized formulation) may be used, or the kallikrein inhibitor may be provided in a device configured for automatic reconstitution (e.g., automatic addition of the diluent to the lyophilized formulation), such as the BECTON-DICKINSON BD™ Liquid Dry Injector.

The isolated kallikrein inhibitor can be provided in a kit. In one embodiment, the kit includes (a) a container that contains a composition that includes an isolated kallikrein inhibitor, and (b) informational material that relates to the methods described herein and/or the use of the agents for therapeutic benefit.

In certain embodiments, the kit includes also includes another therapeutic agent. For example, the kit includes a first container that contains a composition that includes the isolated kallikrein inhibitor, and a second container that includes the other therapeutic agent. The isolated kallikrein inhibitor and the other therapeutic agent may be supplied in the same container for use in methods in which the kallikrein inhibitor and the therapeutic agent are administered as a single composition.

The informational material of the kits is not limited in its form. In one embodiment, the informational material can include information about production of the compound, molecular weight of the compound, concentration, date of expiration, batch or production site information, and so forth. In one embodiment, the informational material relates to methods of administering the isolated kallikrein inhibitor, e.g., in a suitable dose, dosage form, or mode of administration (e.g., a dose, dosage form, or mode of administration described herein), to treat a subject ( ). The information can be provided in a variety of formats, include printed text, computer readable material, video recording, or audio recording, or a information that provides a link or address to substantive material.

In addition to the isolated kallikrein inhibitor (and, if present, the additional therapeutic agent(s)), the composition in the kit can include other ingredients, such as a solvent or buffer, a stabilizer, or a preservative. The isolated kallikrein inhibitor (and other therapeutic agent, if present) can be provided in any form, e.g., liquid, dried or lyophilized form, preferably substantially pure and/or sterile. When the agents are provided in a liquid solution, the liquid solution preferably is an aqueous solution. When the agents are provided as a dried form, reconstitution generally is by the addition of a suitable solvent. The solvent. e.g., sterile water or buffer, can optionally be provided in the kit.

The kit can include one or more containers for the composition or compositions containing the agents. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of the agents. The containers can include a combination unit dosage, e.g., a unit that includes both the isolated kallikrein inhibitor and another therapeutic agent, e.g., in a desired ratio. For example, the kit includes a plurality of syringes, ampoules, foil packets, blister packs, or medical devices, e.g., each containing a single combination unit dose. The containers of the kits can be air tight, waterproof (e.g., impermeable to changes in moisture or evaporation), and/or light-tight.

The kit optionally includes a device suitable for administration of the composition, e.g., a syringe or other suitable delivery device. The device can be provided pre-loaded with one or both of the agents or can be empty, but suitable for loading.

EXAMPLES

The following examples provide further illustration and are not limiting.

Example 1: Association Between Cleaved High Molecule Weight Kininogen (HMWK) and Autoimmune Diseases To determine the levels of cleaved HMWK in autoimmune diseases, the amounts of intact and cleaved HMWK in plasma samples obtained from patients of rheumatoid arthritis (RA), ulcerative colitis (UC), and Crohn's disease (CD), as well as from healthy subjects, were measured using Western blot with LiCor detection as described below.

(i) Sample Preparation

The treated HMWK-deficient plasma was prepared by adding 10 µL of 10× anti-protease inhibitor cocktail to 90 µL 100% HMWK-deficient plasma. The solution was allowed to sit for at least 30 minutes prior to use.

A 1:4 intermediate of the single-chain HMWK was prepared by adding 5 µL of the stock solution (1.61 mg/mL) to 15 µL of treated HMWK-deficient plasma. A 1:4 intermediate of the two-chain HMWK was prepared by adding 5 µL of the stock solution (2.01 mg/mL) to 15 µL of treated HWMK-deficient plasma.

A 45 µg/mL treated HMWK-deficient control plasma solution was prepared by adding 3.35 µL of the 1:4 single-chain HMWK intermediate and 2.69 µL of the 1:4 two-chain HWMK intermediate to 23.96 µL of treated HWMK-deficient plasma.

Each sample was diluted to 5% plasma (1:20) in 1×TBS by adding 5 µL of the plasma sample to 95 µL of 1×TBS. The non-reduced samples were prepared by adding 5 µL of 4× sample buffer to 15 µL of 5% sample. The reduced samples were prepared by adding 5 µL of the 4× sample buffer and 2 µL of 10× reducing agent to 13 µL of 5% sample.

All of the samples were heated at 95° C. for 5 minutes using a heat block. Each sample was briefly centrifuged to remove any solution from the cap of the sample tubes.

(ii) Gel Loading, Running, and Transfer

Tris-Acetate running buffer was prepared by adding 100 mL of 20× running buffer to 1.900 mL of DI water. A volume of 4 µL of the one-color protein marker was used as a control in all assays. A volume of 13 µL of non-reduced samples and the reduced samples was added to lanes of a gel, of gel 1. The gels were run at 125 volts for −2 hours.

The iBlot Filter Paper was placed in DI water and soaked for 5 minutes. The Anode Stack, Bottom was unsealed and placed on the blotting surface of the iBlot with the copper side down. Upon completion of the gel runs, two gel cassettes were opened and the gels removed. The gels were placed onto the transfer membrane. The pre-soaked filter paper was placed on top of the gels. The Cathode Stack, Top was unsealed and placed on top of the filter paper, with the copper side up. The bubbles in the stack were gently rolled out using the blotting roller. The disposable sponge was placed into the iBlot lid. The iBlot was turned on and program P0 was selected.

Upon completion of the iBlot transfer, opened the iBlot and discarded the sponge, cathode stack, and gels. Each membrane was individually removed from the iBlot and placed it into a plastic tray containing 20 mL of Odyssey Blocking Buffer. The membranes were incubated on a plate shaker at room temperature for 1 hour.

(iii) Westernblot Assay with LiCor Detection

A 1 µg/mL primary antibody solution was prepared by adding 57.14 µL of Mouse antiLC HMWK, clone #11H05 (stock concentration 1.4 mg/mL) to 80 mL of Odyssey Blocker+0.2% TWEEN® 20 (Polysorbate 20). The blocking buffer was removed from the plastic trays. A volume of 20 mL of primary antibody solution was added to each tray and the membranes were incubated on a plate shaker at room temperature for 1 hour. The Goat anti-mouse IgG IRDye 680 solution was prepared at a 1:15,000 dilution by adding 5.33 µL of the stock solution to 80 mL of Odyssey Blocker+0.2% TWEEN® 20 (Polysorbate 20). The primary antibody solution was removed from the plastic trays. The membranes were washed with 20 mL 1×PBS+ 0.1% TWEEN® 20

(Polysorbate 20) for five minutes and then the wash was discarded. Repeated 3 times for a total of 4 washes. A volume of 20 mL of the Goat anti-Mouse IgG IRDye 680 solution was added to each tray. The trays were covered with aluminum foil to protect the membranes and the secondary antibody solution from light. The membranes were incubated on a plate shaker at room temperature for 1 hour. The secondary antibody solution was removed from the plastic trays. The membranes were washed with 20 mL 1×PBS+ 0.1% TWEEN® 20 (Polysorbate 20) for five minutes and then the wash was discarded. Repeated 3 times for a total of 4 washes. The membranes were washed with PBS and scanned on the LiCor Odyssey CLx. The membranes were covered with aluminum foil and allowed to dry overnight. The dried membranes were placed in a protective cover sheet and saved for later use.

(iv) Results:

The control, treated HMWK-deficient plasma spiked with 45 µg/mL of single and two-chain HMWK, performed as expected producing banding around 120 and 95 kDa. The normal human plasma produced bands around 120 and 100 kDa with 21.3% of the HMWK cleaved. Patient samples containing anti-protease inhibitor cocktails produced dramatically different results than patient samples collected in sodium citrate. The patient samples collected with anti-protease inhibitor added contained significantly more single-chain HMWK than reduced two-chain HMWK. This result indicates that the addition of anti-protease inhibitor cocktails is necessary to prevent the cleavage of HMWK after collection.

Plasma samples from a number of UC, CD, RA, and HAE patients were examined in this study. The control sample and normal human plasma produced the expected results. The HAE attack sample contained more cleaved HWMK than the HAE basal sample. As shown in Table 1 below and also in FIG. 1, a large majority of the samples from the autoimmune patients, especially the rheumatoid arthritis samples, only produced banding at 46 kDa, indicating that the level of cleaved HWMK is associated with autoimmune diseases, such as RA, UC, and CD. More specifically, RA flares were found to be associated with extensive cleaved HMWK; Crohn's disease was found to has a moderate amount of cleaved HMWK; and ulcerative colitis was found to have a moderate amount of cleaved HMWK.

In sum, the results of this study indicate contact activation in autoimmune diseases such as CD, UC, and RA plasma. Accordingly, an agent that inhibits contact activation, such as an inhibitor of pKal (e.g., those described herein) can be effective in treating such diseases. Further, the results of this study indicate that the level of cleaved HMWK can serve as a reliable biomarker for identifying patients having or at risk for autoimmune diseases such as CD, UC, and RA and/or as a biomarker for assessing the efficacy of an treatment for such an autoimmune disease.

TABLE 1

Levels of cleaved HMWK in RA, UC, and CD Patients

| UID | Age | Gender | Medications | Diagnosis | Disease Stage | % Cleaved HMWK |
| --- | --- | --- | --- | --- | --- | --- |
| 106659 | 34 | Male | Pentasa 500 mg | Crohn's Disease, High cholesterol | Flare | 3 |
| 104006 | 50 | Female | Pentasa 500 mg | Crohn's Disease | Stable | 12.2 |
| 100929 | 59 | Male | Ciproflaxacin, Flagyl | Crohn's Disease | Stable | 32.7 |
| 118166 | 62 | Male | Tinidazole 500 mg | Crohn's disease | Stable | 10.3 |
| 105772 | 22 | Female | Lialda | Crohn's disease | Stable | 95.7 |
| 72211 | 53 | Female | Canasa suppositories, Vitamin C | Ulcerative Colitis | Stable | 13.1 |
| 96319 | 78 | Male | Asacol, Canasa, Hydrocortisone, Prilosec, Tylenol, ASA, Diltazem, Lorazepam, Align probiotic, Vitamins | Ulcerative colitis | Stable | 4.4 |
| 93587 | 24 | Female | Canasa suppositories, Carafate, Omeprazole, Asacol, Remicade | Ulcerative colitis | Stable | 100 |
| 92122 | 21 | Female | Prednisone, Lialda, Remicade, Percocet | Ulcerative colitis | Stable | 4.9 |
| 94441 | 77 | Male | Lialda, Plavix | Ulcerative colitis | Flare | 16.5 |
| 147603 | 72 | Female | Enbrel, Arava 20 mg, Folic acid 1 mg, Azelphadine 500 mg, Synthroid .175 mg, | Rheumatoid Arthritis (flare), 4 out of 5 patients at 100% | Flare | 100 |
| 100953 | 50 | Female | Plaquenil, Meloxicam, MTX, Prednisone | Rheumatoid Arthritis (RA), Hypertension (HTN), Bursitis | Flare | 100 |
| 72015 | 36 | Female | Methotrexate; Folic acid; MVI; Calcium and vitamin D; Prednisone | Rheumatoid Arthritis (RA) | Flare | 100 |
| 31567 | 49 | Female | Enbrel; Tylenol; Medrol; Prilosec; Citalopram; HCT; Fish oil; Naprosyn | Rheumatoid Arthritis (RA) | Flare | 100 |
| 33503 | 44 | Female | Synthroid; Orencia; Prednisone; Ambien; Methotrexate; Hydrocodone; Folic acid | Rheumatoid Arthritis (RA) | Flare | 46.2 |

REFERENCES

The contents of all cited references including literature references, issued patents, published or non-published patent applications cited throughout this application as well as those listed below are hereby expressly incorporated by reference in their entireties for the purposes or subject matter referenced herein. In case of conflict, the present application, including any definitions herein, will control.

EQUIVALENTS AND SCOPE

Those skilled in the art will recognize, or be able to ascertain using no more than routine experimentation, many equivalents to the specific embodiments of the present disclosure described herein. The scope of the present disclosure is not intended to be limited to the above description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The present disclosure includes embodiments in which exactly one member of the group is present in, employed in, or otherwise relevant to a given product or process. The present disclosure includes embodiments in which more than one, or all of the group members are present in, employed in, or otherwise relevant to a given product or process.

Furthermore, the present disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the present disclosure, or aspects of the present disclosure, is/are referred to as comprising particular elements and/or features, certain embodiments of the present disclosure or aspects of the present disclosure consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the present disclosure, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment of the present disclosure can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present disclosure, as defined in the following claims.

---

What is claimed is:

1. A method of treating an autoimmune disease in a subject, the method comprising administering to a subject in need thereof an effective amount of a plasma kallikrein (pKal) inhibitor, an anti-inflammatory agent, or a combination thereof,
   wherein the subject has an elevated level of cleaved high molecular weight kininogen (HMWK) as compared to a healthy subject in one or more biological samples of the subject,
   wherein the one or more biological samples are blood samples, serum samples, or plasma samples;
   wherein the subject is a human subject having or suspected of having the autoimmune disease, which is rheumatoid arthritis (RA), Crohn's disease (CD), or ulcerative colitis (UC).

2. The method of claim 1, wherein the subject is administered a pKal inhibitor.

3. The method of claim 2, wherein the pKal inhibitor is a Kunitz domain polypeptide or an antibody binding to pKal.

4. The method of claim 2, wherein the pKal inhibitor is DX-2930, DX-88, or EPIKAL-2.

5. The method of claim 1, wherein the subject is administered an anti-inflammatory agent, which is a steroid or a nonsteroidal anti-inflammatory drug (NSAID).

6. A method of treating an autoimmune disease, the method comprising:

(i) identifying a subject as having or at risk for an autoimmune disease based on the level of cleaved high molecular weight kininogen (HMWK), wherein the subject has an elevated level of cleaved HMWK as compared to a healthy subject, in one or more biological samples of the subject; and (ii) administering to the subject an effective amount of a plasma kallikrein (pKal) inhibitor, an anti-inflammatory agent, or a combination thereof,
   wherein the one or more biological samples are blood samples, serum samples, or plasma samples;
   wherein the subject is a human subject having or suspected of having the autoimmune disease, which is rheumatoid arthritis (RA), Crohn's disease (CD), or ulcerative colitis (UC).

7. The method of claim 6, wherein the subject is administered a pKal inhibitor.

8. The method of claim 7, wherein the pKal inhibitor is a Kunitz domain polypeptide or an antibody binding to pKal.

9. The method of claim 8, wherein the pKal inhibitor is DX-2930, DX-88, or EPIKAL-2.

10. The method of claim 6, wherein the subject is administered an anti-inflammatory agent, which is a steroid or a nonsteroidal anti-inflammatory drug (NSAID).

* * * * *